(12) United States Patent
Yildirim

(10) Patent No.: US 11,410,769 B1
(45) Date of Patent: Aug. 9, 2022

(54) TACTILE SOLUTIONS INTEGRATION FOR PATIENT SPECIFIC TREATMENT

(71) Applicant: VENT CREATIVITY CORPORATION, Weehawken, NJ (US)

(72) Inventor: Gokce Yildirim, Weehawken, NJ (US)

(73) Assignee: VENT CREATIVITY CORPORATION, Weehawken, NJ (US)

(*) Notice: Subject to any disclaimer, the term of this patent is extended or adjusted under 35 U.S.C. 154(b) by 0 days.

(21) Appl. No.: 17/545,453

(22) Filed: Dec. 8, 2021

(51) Int. Cl.
*G16H 20/40* (2018.01)
*G06T 19/20* (2011.01)
(Continued)

(52) U.S. Cl.
CPC ........... *G16H 20/40* (2018.01); *A61B 34/10* (2016.02); *G06F 3/014* (2013.01); *G06N 3/08* (2013.01); *G06T 7/0012* (2013.01); *G06T 19/20* (2013.01); *G16H 30/20* (2018.01); *A61B 34/32* (2016.02); *A61B 2034/102* (2016.02); *A61B 2034/105* (2016.02); *A61B 2034/107* (2016.02); *A61B 2034/108* (2016.02); *G06T 2207/20081* (2013.01); *G06T 2207/20084* (2013.01); *G06T 2219/2004* (2013.01)

(58) Field of Classification Search
CPC ........ G16H 20/40; G16H 30/20; A61B 34/10; A61B 2034/102; A61B 2034/105; A61B 2034/107; A61B 2034/108; A61B 34/32; G06F 3/014; G06N 3/08; G06T 7/0012; G06T 19/20; G06T 2207/20081; G06T 2207/20084; G06T 2219/2004
See application file for complete search history.

(56) References Cited

U.S. PATENT DOCUMENTS 9,452,050 B2 9/2016 Miles et al.
10,292,770 B2 5/2019 Ryan et al.
(Continued)

FOREIGN PATENT DOCUMENTS

EP 1716535 A2 11/2006
EP 2754419 A2 7/2014
(Continued)

*Primary Examiner* — Brenda C Bernardi
(74) *Attorney, Agent, or Firm* — Dave Law Group LLC; Raj S. Dave

(57) ABSTRACT

Embodiments related to a method is described. The method comprises receiving an image file of a region of interest of an anatomy of a living organism, analyzing the image file and extracting image coordinates and density information of a plurality of points in the image file, training a neural network using collective information available in a database, registering the region of interest of the anatomy as a virtual version using an input from the neural network, and subsequently training the neural network using a user input from a user and the collective information available in the database. The collective information is recorded in the database with respect to a plurality of clusters of different physiological states of the living organism. The method further comprises performing a treatment on the region of interest. In an embodiment, the treatment is performed using the input from the neural network.

18 Claims, 13 Drawing Sheets

(51) Int. Cl.
*G06F 3/01* (2006.01)
*G06N 3/08* (2006.01)
*G16H 30/20* (2018.01)
*A61B 34/10* (2016.01)
*G06T 7/00* (2017.01)
*A61B 34/32* (2016.01)

(56) References Cited

U.S. PATENT DOCUMENTS

| | | |
|---|---|---|
| 10,582,970 B2 | 3/2020 | Yildirim et al. |
| 10,595,844 B2 | 3/2020 | Nawana et al. |
| 2008/0221923 A1 | 9/2008 | Shogan |
| 2010/0251117 A1* | 9/2010 | Baughman ............. G06N 3/006 703/11 |
| 2014/0093153 A1 | 4/2014 | Sofka et al. |
| 2015/0328004 A1 | 11/2015 | Mafhouz |
| 2017/0148213 A1* | 5/2017 | Thomas ................. G06T 19/003 |
| 2018/0369611 A1* | 12/2018 | Owens ................. A61N 5/1064 |
| 2019/0005186 A1 | 1/2019 | Nikou et al. |
| 2019/0183411 A1 | 6/2019 | Yildirim et al. |
| 2019/0192880 A1* | 6/2019 | Hibbard ................ A61N 5/1039 |
| 2019/0333623 A1* | 10/2019 | Hibbard ................ G06N 3/088 |
| 2020/0170604 A1 | 6/2020 | Yildirim et al. |
| 2020/0178885 A1* | 6/2020 | Orr .......................... A61B 5/00 |

FOREIGN PATENT DOCUMENTS

| | | |
|---|---|---|
| WO | 2020037308 A1 | 2/2020 |
| WO | 2020141812 A1 | 7/2020 |

\* cited by examiner

TACTILE SOLUTIONS INTEGRATION FOR PATIENT SPECIFIC TREATMENT

FIELD OF THE INVENTION

This disclosure relates to patient specific treatment planning, and more particularly to assisting in treatment planning, and pre-treatment and post-treatment recovery tracking.

BACKGROUND

"Systems and methods for generating a surgical plan for altering an abnormal bone using a generic normal bone model are discussed. For example, a system for planning a surgery on an abnormal bone can include a model receiver module configured to receive a generic normal bone model. The generic normal bone model, such as a parametric model derived from statistical shape data, can include a data set representing a normal bone having an anatomical origin comparable to the abnormal bone. An input interface can be configured to receive an abnormal bone representation including a data set representing the abnormal bone. A surgical planning module can include a registration module configured to register the generic normal bone model to the abnormal bone representation by creating a registered generic model. A surgical plan formation module can be configured to identify one or more abnormal regions of the abnormal bone using the registered generic model." [Source: Systems and methods for using generic anatomy models in surgical planning; Constantinos Nikou, Branislav Jaramaz; published as US20190005186A1 on 3 Jan. 2019].

"Methods and devices are disclosed relating improved articular models, implant components, and related guide tools and procedures. In addition, methods and devices are disclosed relating articular models, implant components, and/or related guide tools and procedures that include one or more features derived from patient-data, for example, images of the patient's joint. The data can be used to create a model for analyzing a patient's joint and to devise and evaluate a course of corrective action. The data also can be used to create patient-adapted implant components and related tools and procedures." [Source: Patient-adapted and improved orthopedic implants, designs and related tools; Raymond A. Bojarski, Nam Chao, John Slamin, Thomas Minas, Philipp Lang, Wolfgang Fitz, Daniel Steines, Terrance Wong; published as EP2754419A2 on 16 Jul. 2014].

"[t]he automatic bone segmentation may also include automatic segmentation of metal structures in the target joint area. In an advantageous implementation, metal structures are automatically segmented in the medical image data using intensity thresholding. Metal appears very bright in CT images and can therefore be accurately differentiated from bone structures and other tissue by extracting voxels having an intensity above a certain threshold." [Source: Method and System for Bone Segmentation and Landmark Detection for Joint Replacement Surgery; Michal Sofka, Meizhu Liu, Dijia Wu, Shaohua Kevin Zhou; published as US20140093153A1 on 3 Apr. 2014].

"Various systems and methods are provided for surgical and interventional planning, support, post-operative follow-up, and functional recovery tracking. In general, a patient can be tracked throughout medical treatment including through initial onset of symptoms, diagnosis, non-surgical treatment, surgical treatment, and recovery from the surgical treatment. In one embodiment, a patient and one or more medical professionals involved with treating the patient can electronically access a comprehensive treatment planning, support, and review system. The system can provide recommendations regarding diagnosis, non-surgical treatment, surgical treatment, and recovery from the surgical treatment based on data gathered from the patient and the medical professional(s). The system can manage the tracking of multiple patients, thereby allowing for data comparison between similar aspects of medical treatments and for learning over time through continual data gathering, analysis, and assimilation to decision-making algorithms." [Source: Systems and methods for surgical and interventional planning, support, post-operative follow-up, and functional recovery tracking; Namal Nawana, William C. Horton, William J. Frasier, Cody Cranson, Max Reinhardt, Mark T. Hall, Matthew Parsons, Jennifer DiPietro, Kevin Lee, Michelle LaWare, John P. Griffin, Sean P. Selover, Jonathan Bellas, Douglas Raymond, Nicholas Pavento, Mary L. Fowler, Dennis Chien; published as U.S. Ser. No. 10/595,844B2 on 24 Mar. 2020].

FIG. 1 illustrates a traditional process of segmentation that recognizes a segment of a region of interest of an image as a bone based on a single predefined threshold value, according to a prior art. The traditional process of segmentation, described herein, assigns the single predefined threshold value to the region of interest. The traditional process of segmentation analyses the segment of the region of interest and when a Hounsfield unit of the segment of the region of interest is above the single predefined threshold value, then the segment of the region of interest is recognized and/or categorized as the bone. However, the traditional process of segmentation is not able to separate and depict two fused bones of different density values (as depicted in 102). In the traditional process of segmentation, the region of interest is assigned with the single predefined threshold value. Further as resolution of the image is low, the traditional process of segmentation is not capable to separate two fused bones. At 102, the two bones of different density values are fused and shown together, where a user is not able to readily identify and analyze different segments (e.g., bones) present in the region of interest.

"A method of preparing a joint for a prosthesis in a patient. The method includes obtaining scan data associated with the joint of the patient, preparing a three-dimensional image of the joint based on the scan data, preparing an interactive initial surgical plan based on the scan data, sending the surgical plan to a surgeon, receiving a finalized surgical plan from the surgeon, and preparing an image of a patient-specific alignment guide." [Source: Patient Specific Knee Alignment Guide and Associated Method; Robert Metzger; Keith R. Berend, Michael E. Berend, Adolph V. Lombardi, Lance D. Perry, Ryan J. Schoenefeld; published as US20070288030A1 on Dec. 13, 2007]

"FIGS. 25A, 25B and 25C [, in the prior art,] are different views of surgical gloves by which at least aspects of surgical navigation may be implemented, arranged in accordance with at least some embodiments described herein. FIG. 25A [, in the prior art,] shows an example unaided view 2500 of surgical gloves. FIG. 25B [, in the prior art,] shows an example headset view 2505 of a visible surgical glove 2510 manipulating a virtual object 2515. FIG. 25C [, in the prior art,] shows an example headset view 2520 of an invisible surgical glove manipulating a virtual object. In these examples, the gloves may be visualized using a projected dot matrix if desired. Alternatively, the gloves may be modified with a registration stripe on each finger, and optionally an RFID antenna tag near the fingernail of each finger and on the boney prominence of the scaphoid bone, medial and distal to the radius at the wrist so as to quickly convey a gesture command language." [Source: Systems and methods for assisted surgical navigation; Justin Esterberg; published as US20160324580A1 on Nov. 10, 2016].

Therefore, there is a long felt need to identify, locate, and depict bones of different density values. Further, there is a long-felt need for a system for performing patient specific treatment planning based on density, multi-thresholding and kinematics associated with the region of interest. Further, there is a long felt need for an alignment guide that fits exactly at the region of interest providing exact alignment, as well as having tools to hold external instruments and render virtual measurements to assist the surgeon while providing the treatment. Further, there is also a long felt need for a surface compliance device for medical imaging without any intruding rays.

SUMMARY OF INVENTION

Disclosed herein are methods and systems of assisting in providing treatment to a patient and pre-treatment and post-treatment recovery tracking.

In one aspect, a method is described. The method comprises receiving an image file of a region of interest of an anatomy of a living organism, analyzing the image file and extracting image coordinates and density information of a plurality of points in the image file, training a neural network using collective information available in a database, registering the region of interest of the anatomy as a virtual version using an input from the neural network, and subsequently training the neural network using a user input from a user and the collective information available in the database. The collective information is recorded in the database with respect to a plurality of clusters of different physiological states of the living organism.

In an embodiment, the method further comprises performing a treatment on the region of interest using the input from the neural network.

In another embodiment, the method further comprises recording the image coordinates and the density information of the region of interest in the database, recording first information into the database based on at least one of performing a treatment and a registration of the region of interest under a first cluster of the plurality of clusters of different physiological states to which the region of interest belongs, and recording second information into the database, under the first cluster of the plurality of clusters of different physiological states to which the region of interest belongs, based on at least one of an outcome of the treatment and a feedback from the user.

In yet another embodiment, recording the second information into the database comprises updating the first information based on at least one of the outcome of the treatment, and the feedback from the user.

In yet another embodiment, the feedback from the user comprises at least one of confirmation and declaration from the user that the region of interest belongs to a cluster among the plurality of clusters of different physiological states.

In yet another embodiment, extracting the image coordinates and the density information of the plurality of points comprises: creating point cloud information of the anatomy based on the image coordinates, the density information, and the collective information.

In yet another embodiment, creating the point cloud information of the anatomy comprises generating a heat map of the anatomy based on the point cloud information.

In yet another embodiment, the heat map indicates a location of a first bone, a second bone, a first object, a second object, soft tissues, hemorrhage, blockage, cancerous cells, and a foreign object within the region of interest.

In yet another embodiment, generating the heat map indicating the location of the first bone, the second bone, the soft tissues, the hemorrhage, the blockage, the cancerous cells, and the foreign object comprises: automatically assigning a threshold value to at least one of an object and a segment within the region of interest.

In yet another embodiment, automatically assigning the threshold value to at least one of the object and the segment within the region of interest comprises: automatically assigning the threshold value for the object within the region of interest based on the density information of the object.

In yet another embodiment, registering the region of interest as the virtual version comprises performing at least one of segmenting a segment of the region of interest, landmarking the segment of the region of interest, labelling the segment of the region of interest, and creating a treatment plan for the region of interest.

In yet another embodiment, registering the region of interest as the virtual version further comprises: recommending at least one of a treatment procedure, the treatment plan, and a treatment location of the region of interest based on the collective information in the database.

In yet another embodiment, recommending at least one of the treatment procedure, the treatment plan, and the treatment location of the region of interest based on the collective information in the database comprises: creating the treatment plan to at least one of reach and approach one of an area of interest and an object within the region of interest in six degrees of freedom with a variable path through at least one of invasive route, and partially invasive route, and recommending the treatment plan to at least one of an automated machine, a semi-automated machine, and a surgeon to perform the treatment.

In yet another embodiment, creating the treatment plan comprises: automatically generating a path, by the neural network, which guide one of the automated machine, the semi-automated machine, and the surgeon to at least one of reach and approach one of the area of interest and the object within the region of interest. The path comprises at least one of a straight path, a regular path, a curved path, and an irregular path.

In yet another embodiment, the path is generated in compliance to engineering safety rules and surgeon prescribed rules.

In yet another embodiment, the method further comprises: training the neural network using the engineering safety rules and the surgeon prescribed rules to generate the path to at least one of reach and approach one of the area of interest and the object within the region of interest.

In yet another embodiment, the method further comprises: recording the engineering safety rules and the surgeon prescribed rules into the database with respect to the region of interest under respective cluster of the plurality of clusters of different physiological states and updating the engineering safety rules and the surgeon prescribed rules into the database when there is change in the engineering safety rules and the surgeon prescribed rules.

In yet another embodiment, segmenting the segment of the region of interest comprises: generating a heat map based on point cloud information of the anatomy, assigning a threshold value to the segment of the region of interest, estimating a predefined measurement unit of the plurality of points of the image file, outlining the segment of the region of interest, and determining at least one of an edge, a boundary, and a tunnel of the region of interest based on the predefined measurement unit.

In yet another embodiment, the predefined measurement unit comprises Hounsfield units.

In yet another embodiment, determining at least one of the edge, the boundary, and the tunnel of the region of interest based on the predefined measurement unit comprises: determining density value of the plurality of points of the region of interest, and determining a plurality of first points on the region of interest as at least one of the edge, the boundary, and the tunnel, when a first density value of the plurality of first points is one of greater than and less than a second density value of a plurality of second points. The plurality of second points is located on one of either side, adjacent, and in between the plurality of first points.

In yet another embodiment, landmarking the segment of the region of interest comprises identifying a ligament attachment point and a tendon attachment point on the region of interest and creating planes and lines to the region of interest.

In yet another embodiment, landmarking the segment of the region of interest comprises identifying a cluster among the plurality of clusters of different physiological states to which the region of interest belongs, correlating a virtual kinematic model of the region of interest with a predefined virtual kinematic model of the cluster identified, analyzing motion of the virtual kinematic model and predicting a constraint and a constraint location for the virtual kinematic model, determining a first position and a first angle for at least one of a ligament attachment point, and a tendon attachment point in the virtual kinematic model at a first level, and determining a second position and a second angle for at least one of the ligament attachment point and the tendon attachment point in the virtual kinematic model at a second level, when the first position and first angle fails to create an optimum kinematics in the virtual kinematic model.

In yet another embodiment, landmarking the segment of the region of interest comprises categorizing information associated with the region of interest under a sub-cluster of the cluster based on at least one of the ligament attachment point, and the tendon attachment point.

In yet another embodiment, the collective information comprises at least one of pre-stored information, the image coordinates, and the density information of the region of interest, first information recorded based on a registration of the region of interest as the virtual version, and a treatment performed on the region of interest, and second information recorded based on at least one of outcome of the treatment, and a feedback from the user.

In yet another embodiment, recording the first information on the database comprises recording remarks information indicating at least one of a first outcome, and a second outcome of a treatment while performing one of the treatment and the registration of the region of interest as the virtual version.

In yet another embodiment, recording the remarks information comprises recording a plurality of first parameters, and a plurality of second parameters that contribute to the first outcome and the second outcome, respectively.

In yet another embodiment, the plurality of clusters of different physiological states comprises a first cluster, and a second cluster.

In yet another embodiment, the plurality of clusters of different physiological states comprises at least one of a third cluster based on landmarks of the region of interest, a fourth cluster based on a tendon attachment point, and a fifth cluster based on a ligament attachment point of the region of interest.

In yet another embodiment, the pre-stored information comprises information with respect to a first cluster, a second cluster, a third cluster, a fourth cluster, a fifth cluster and a sixth cluster.

In yet another embodiment, the pre-stored information comprises at least one of a predefined virtual kinematic model, a predefined treatment location, a predefined treatment procedure, a predefined treatment plan, a predefined route, and a path to reach an area of interest within the region of interest, and predefined density information.

In yet another embodiment, creating the treatment plan for the region of interest comprises: analyzing a defect on the region of interest, simulating a virtual kinematic model of the region of interest, identifying a cluster from the plurality of clusters of different physiological states to which the region of interest belongs, correlating the virtual kinematic model with a predefined virtual kinematic model of the cluster identified, analyzing motion of the virtual kinematic model and predicting a constraint and a constraint location for the virtual kinematic model, and creating at least one of a treatment procedure, the treatment plan, a tendon attachment point, and a ligament attachment point for the region of interest.

In yet another embodiment, identifying the cluster from the plurality of clusters of different physiological states to which the region of interest belongs comprises: recording information associated with the region of interest under a new cluster when the region of interest is beyond the cluster among the plurality of clusters of different physiological states, the new cluster comprises a sub-cluster.

In yet another embodiment, creating the treatment plan comprises: recovering kinematics and retaining an activity of daily living (ADL) of the living organism.

In yet another embodiment, retaining the activity of daily living comprises: retaining the activity of daily living by recovering the kinematics of the region of interest back to the cluster identified, and retaining the activity of daily living by recovering the kinematics of the region of interest back to a second cluster, when retaining the ADL to the cluster identified is at least one of failed and flawed.

In yet another embodiment, retaining the activity of daily living comprises: retaining the activity of daily living by performing a regression analysis based on the collective information in the database.

In yet another embodiment, labelling the segment of the region of interest comprises: labelling the segment of the region of interest based on at least one of the density information and the image coordinates.

In yet another embodiment, the plurality of clusters of different physiological states comprises a plurality of sub-clusters.

In yet another embodiment, the collective information comprises the plurality of clusters of different physiological states with respect to age, gender, race, geographic location, and morphology.

In yet another embodiment, assigning the threshold value to the segment of the region of interest comprises: identifying the segment within the region of interest based on the image coordinates, and the density information, and assigning the threshold value to the segment within the region of interest.

In yet another embodiment, the living organism comprises an animal, a bird, a mammal, and a human being.

In yet another embodiment, the user comprises at least one of a surgeon, a physician, a caretaker, a medical practitioner, and a machine.

In yet another embodiment, the machine comprises at least one of an automated machine, a navigation tracking device, a robot, and a semi-automated machine.

In yet another embodiment, receiving the image file of the region of interest of the anatomy comprises receiving the image file of the region of interest as a Digital Imaging and Communications in Medicine (DICOM) format file.

In yet another embodiment, retaining the activity of daily living by recovering the kinematics of the region of interest back to one of the cluster identified and the second cluster comprises: recovering the kinematics with a compensation factor and estimating a return score to one of the cluster identified, and the second cluster.

In yet another embodiment, registering the region of interest as the virtual version further comprises performing a treatment virtually on the virtual version.

In yet another embodiment, performing the treatment virtually on the virtual version comprises: analyzing outcome of the treatment on the region of interest, and updating the collective information recorded into the database.

In yet another embodiment, wherein analyzing the outcome of the treatment on the region of interest comprises at least one of analyzing kinematics and motion associated with the region of interest, analyzing functioning of the region of interest, and analyzing defects on the region of interest.

In yet another embodiment, the method further comprises: communicating wirelessly the collective information, and one of a processed image output and a processed video output of the virtual version to a device associated with the user.

In yet another embodiment, registering the region of interest as the virtual version comprises: registering the region of interest as the virtual version through at least one of a virtual reality and an augmented reality environment.

In yet another embodiment, performing the treatment on the region of interest comprises: performing the treatment on the region of interest through at least one of a virtual reality and an augmented reality environment.

In yet another embodiment, registering the region of interest as the virtual version comprises: generating at least one of a three-dimensional (3D) virtual kinematic model of the region of interest and a processed image file of the region of interest based on the image coordinates, the density information, and the collective information of the database, simulating the three-dimensional (3D) virtual kinematic model to virtually display functioning of the region of interest to the user, and assisting the user to perform a treatment on the region of interest.

In yet another embodiment, assisting the user to perform the treatment on the region of interest comprises depicting a treatment procedure on the region of interest.

In yet another embodiment, depicting the treatment procedure on the region of interest comprises at least one of displaying density point clouds, a boundary on the region of interest, indicating a virtual cut on the region of interest, and indicating a position of screws on the region of interest. The treatment procedure guides the user to perform an intervention within the boundary and restricted area during the treatment.

In yet another embodiment, generating at least one of the three-dimensional (3D) virtual kinematic model and the processed image file of the region of interest comprises indicating a first feature in a first color and a first identifier and a second feature in a second color and a second identifier, respectively.

In yet another embodiment, generating at least one of the three-dimensional (3D) virtual kinematic model of the region of interest and the processed image file of the region of interest comprises: enabling at least one of an automated machine, and a semi-automated machine to print a three-dimensional (3D) physical incarnation of at least one of the processed image file and the three-dimensional (3D) virtual kinematic model of the region of interest.

In yet another embodiment, generating at least one of the three-dimensional (3D) virtual kinematic model of the region of interest and the processed image file of the region of interest comprises enabling at least one of an automated machine, and a semi-automated machine to provide a virtual reality version and an augmented reality version of the three-dimensional (3D) virtual kinematic model and the processed image file.

In yet another embodiment, providing the virtual reality version and the augmented reality version of the three-dimensional (3D) virtual kinematic model and the processed image file comprises enabling the user to perform the treatment on the region of interest through one of remotely and directly.

In yet another embodiment, printing the three-dimensional physical incarnation of at least one of the processed image file, and the three-dimensional (3D) virtual kinematic model of the region of interest comprises: indicating a first feature of the three-dimensional physical incarnation with a first color and a first identifier, and a second feature of the three-dimensional physical incarnation with a second color and a second identifier.

In yet another embodiment, indicating the first feature of the three-dimensional physical incarnation with the first color and the first identifier and the second feature of the three-dimensional physical incarnation with the second color and the second identifier comprises: enabling at least one of the automated machine and the semi-automated machine to track the three-dimensional physical incarnation and recognize the first color and the first identifier, and the second color and the second identifier on the three-dimensional physical incarnation.

In yet another embodiment, the method further comprises: generating a virtual surgery generated alignment guide based on tracking the three-dimensional physical incarnation and recognizing the first color and the first identifier, and the second color and the second identifier on the three-dimensional physical incarnation.

In yet another embodiment, the virtual surgery generated alignment guide is a physical alignment guide generated based on a virtual surgery performed on the region of interest.

In yet another embodiment, the method further comprises: generating a virtual version of the virtual surgery generated alignment guide, wherein the virtual version of the virtual surgery generated alignment guide comprises at least one of a two-dimensional virtual surgery generated alignment guide and a three-dimensional virtual surgery generated alignment guide.

In yet another embodiment, the method further comprises: virtually attaching the virtual version of the virtual surgery generated alignment guide to a physiological feature at a first location in the region of interest where a surgical incision has created enough opening to expose medical image predicted surface on the region of interest.

In yet another embodiment, the method further comprises: analyzing, using the neural network, the virtual attachment of the virtual surgery generated alignment guide on the physiological feature, generating a physical version of the virtual surgery generated alignment guide, and physically attaching the virtual surgery generated alignment guide to the physiological feature at the first location in the region of interest based on the analyzing performed.

In yet another embodiment, virtually attaching the virtual surgery generated alignment guide to the physiological feature at the first location in the region of interest is performed based on Digital Imaging and Communications in Medicine (DICOM) image Boolean subtraction.

In yet another embodiment, the medical image predicted surface is exposed using a DICOM image Boolean subtraction.

In yet another embodiment, the virtual surgery generated alignment guide comprises a coupling feature adapted to couple at least one external attachment with the virtual surgery generated alignment guide mechanically and electronically.

In yet another embodiment, the at least one external attachment comprises at least one of a manually operated machine, the automated machine, and the semi-automated machine.

In yet another embodiment, the manually operated machine comprises at least one of a cutting guide, a cutting machine, and a cutting tool.

In yet another embodiment, one of the automated machine and the semi-automated machine comprises at least one of a navigation tracking device, a camera, a sensor, a glove with force sensors, and a measurement tool.

In yet another embodiment, the navigation tracking device is operable to depict a location, and an orientation of the virtual surgery generated alignment guide.

In yet another embodiment, the virtual version of the virtual surgery generated alignment guide appropriately fits the region of interest of the anatomy while attaching the virtual surgery generated alignment guide to a physiological feature of the region of interest.

In yet another embodiment, the virtual version of the virtual surgery generated alignment guide matches physical location of the region of interest.

In yet another embodiment, the virtual version of the virtual surgery generated alignment guide appropriately fitting the region of interest of the anatomy further enables effective and instant registration of a location and an orientation of the region of interest with a second region of interest of the anatomy to the virtual version.

In yet another embodiment, the registration of the location and the orientation of the region of interest with the second region of interest of the anatomy to the virtual version enables the user to be aware of the location, and the orientation of the region of interest.

In yet another embodiment, the at least one external attachment, is coupled with the virtual surgery generated alignment guide through the coupling feature, enables displaying a treatment plan of at least one of indicating a virtual cut, density point clouds, and indicating a position of screws on the region of interest with respect to the at least one external attachment.

In yet another embodiment, the method further comprises: measuring the virtual version of the region of interest using a virtual measurement tool and rendering virtual measurements of the region of interest.

In yet another embodiment, the virtual measurements assist the user to perform a manual surgery where one of a robotic and an automated surgery is used.

In yet another embodiment, the virtual measurements comprise in-depth measurements, and inner diameter of the region of interest.

In yet another embodiment, the in-depth measurements comprise measure of a depth of a k-wire to be drilled down until a posterior end of the region of interest is reached.

In yet another embodiment, the virtual version of the virtual surgery generated alignment guide comprises virtual measurements that enables the user to one of mark surgical measurements and make surgical notes prior to the treatment.

In yet another embodiment, generating the virtual surgery generated alignment guide comprises a slot with an anterior protrusion with an opening to prevent a saw blade from plunging deeper than a length of the anterior protrusion of the region of interest to prevent at least one of soft-tissue damage and artery damage.

In yet another embodiment, the virtual surgery generated alignment guide, comprising the slot with the opening, is generated using a computer aided design (CAD) modelling technique.

In yet another embodiment, enabling at least one of the automated machine, and the semi-automated machine to track the three-dimensional physical incarnation and recognize the first color and the first identifier, and the second color and the second identifier on the three-dimensional physical incarnation comprises enabling at least one of the automated machine and the semi-automated machine to mimic a tool held by the user and perform the treatment remotely as directed by the user.

In yet another embodiment, the tool held by the user comprises a surface compliance device.

In yet another embodiment, the surface compliance device comprises a glove with force sensors.

In yet another embodiment, the force sensors are embedded into tactile fingerprint regions of the glove.

In yet another embodiment, the tool held by the user enables the user to track the three-dimensional physical incarnation and paint a physiological feature of the three-dimensional physical incarnation.

In yet another embodiment, painting the physiological feature of the three-dimensional physical incarnation enables one of generating a computer topography representation of the three-dimensional physical incarnation and selecting a landmark of the three-dimensional physical incarnation.

In yet another embodiment, the tool held by the user enables to determine initial stability, perform post-surgical cuts, and perform one of implant and trial placement to determine stiffness level.

In yet another embodiment, enabling at least one of the automated machine and the semi-automated machine to track the three-dimensional physical incarnation and recognize the first color and the first identifier, and the second color, and the second identifier on the three-dimensional physical incarnation comprises enabling at least one of the automated machine and the semi-automated machine to track a location of a first bone and depict at least one of a potential implant position, a screw position and a plate position for optimum fixation.

In yet another embodiment, enabling at least one of the automated machine and the semi-automated machine to print the three-dimensional physical incarnation of at least one of the processed image file and the three-dimensional (3D) virtual kinematic model of the region of interest comprises: positioning the three-dimensional physical incarnation and performing one of a two-dimensional (2D) spot-check and diagnosis X-rays, and checking one of a pre-op X-ray, a post-op X-ray and 2D image.

In yet another embodiment, wherein generating at least one of the three-dimensional (3D) virtual kinematic model of the region of interest and the processed image file of the region of interest comprises: enabling the user to virtually turn-on and turn-off individual layers of a segment.

In yet another embodiment, generating the physical version of the virtual surgery generated alignment guide comprises a printed tracking feature attached directly on to the virtual surgery generated alignment guide.

In yet another embodiment, the printed tracking feature comprises a colored quick response (QR) code and detectable wave frequency.

In yet another embodiment, the colored quick response (QR) code comprises contrasting colors adapted to distinguish and determine different planes, regions, sides, boundaries, and angles of a shape of the region of interest.

In yet another embodiment, the printed tracking feature is operable to automatically register at least one of an orientation, a location, and a position of the region of interest in relation to the anatomy.

In yet another embodiment, the printed tracking feature provides information, regarding at least one of depth, artery information, veins, tissue, and ligaments of the region of interest scanned using a scanning device.

In yet another embodiment, the printed tracking feature further provides information regarding a tool associated with the virtual surgery generated alignment guide.

In yet another embodiment, the virtual surgery generated alignment guide comprises a first portion, and a second portion.

In yet another embodiment, the first portion is adapted to attach the virtual surgery generated alignment guide exactly to an optimum region on the region of interest.

In yet another embodiment, the first portion is adapted to exactly align the virtual surgery generated alignment guide with respect to the region of interest.

In yet another embodiment, the second portion comprises a first tool adapted to identify and match the region of interest in relation to the anatomy in a medical imaging technique.

In yet another embodiment, the second portion comprises a second tool adapted to at least one of hold and fasten an external instrument.

In yet another embodiment, the external instrument comprises at least one of a semi-automated instrument, an automated instrument, a camera, a navigation tracking device, and a manual instrument.

In yet another embodiment, the external instrument comprises a cutting guide.

In yet another embodiment, the second portion comprises a third tool adapted to at least one of hold and attach an alignment guide.

In yet another embodiment, the alignment guide comprises a tracking tool.

In yet another embodiment, the tracking tool comprises an infrared light tracking device.

In yet another embodiment, the method further comprises: recognizing and identifying a location, a position, and an identity of the region of interest and communicating a signal to a navigation tracking device using the virtually surgery generated alignment guide.

In yet another embodiment, the method further comprises: determining parameters used for performing the treatment on the region of interest using the virtual surgery generated alignment guide.

In yet another embodiment, the method further comprises: communicating the parameters to the navigation tracking device.

In yet another embodiment, the method further comprises: providing instructions to an external equipment by the navigation tracking device while performing the treatment.

In yet another embodiment, the parameters comprise at least one of landmark points, virtual cuts, measurements, information of the region of interest, orientation of the region of interest, the density information of the region of interest, alignment information of the region of interest, depth associated with the region of interest, and structural information of the region of interest.

In yet another embodiment, the structural information comprises a location, a position, a depth, an orientation, and an angle of at least one of an artery, a tissue, a ligament, and a muscle of the region of interest.

In yet another embodiment, the colored quick response (QR) code comprises dimensions of the virtual surgery generated alignment guide, dimensions of the region of interest, angular information of the region of interest, patient specific surgery information, and surgery information updated by a surgeon.

In an aspect, a database is described. The database comprises collective information comprising pre-stored information, image coordinates and density information of a region of interest, first information collected based on registration of the region of interest as a virtual version and a treatment on the region of interest, and second information collected based on an outcome of the treatment and a feedback from a user. The collective information comprises a plurality of clusters of different physiological states of a living organism.

In an embodiment, the second information comprises the first information updated based on at least one of the outcome of the treatment, and the feedback from the user.

In another embodiment, the first information on the database comprises remarks information indicating at least one of a first outcome, and a second outcome of the treatment.

In yet another embodiment, the remarks information comprises a plurality of first parameters and a plurality of second parameters that contributes to the first outcome and the second outcome of the treatment, respectively.

In yet another embodiment, the plurality of first parameters comprises at least one of a treatment procedure, a treatment plan, and a treatment location that contributes to the first outcome.

In yet another embodiment, the plurality of second parameters comprises at least one of a treatment procedure, a treatment plan, and a treatment location that contributes to the second outcome.

In yet another embodiment, the collective information comprises at least one of a processed image output and a processed video output of at least one of the virtual version of the region of interest, and the treatment on the region of interest.

In yet another aspect, a surface compliance device is described. The surface compliance device comprises a force sensor, and a tracking device. The force sensor is operable to generate closed loop information of a region of interest. The tracking device is operable to track at least one of a location and a position of the region of interest where the surface compliance device is in contact with the region of interest.

In an embodiment, the surface compliance device is operable to detect variable loads provided by a user and calibrate the variable loads to various interactions.

In another embodiment, the surface compliance device comprises a glove.

In yet another embodiment, the tracking device is operable to track at least one of the location and the position of the region of interest in relation to an anatomy.

In yet another embodiment, the force sensor is embedded into a tactile region.

In yet another embodiment, the force sensor is operable to calibrate for a user to estimate in-surgery force of the user.

In yet another embodiment, the surface compliance device compares the estimated in-surgery force of the user with a pre-stored in-surgery force of the user to determine at least one of a ligament tension, a constraint in the region of interest, and a tissue stiffness at the region of interest.

In yet another embodiment, the surface compliance device is operable to trace a surface of the region of interest and paint a feature of the region of interest.

In yet another embodiment, the surface compliance device tracing the surface of the region of interest and painting the feature of the region of interest enables at least one of generating a computer topography representation of the region of interest and selecting landmarks of the region of interest.

In yet another embodiment, the surface compliance device is operable to determine at least one of initial stability, post-surgical cuts, and perform one of implant and trial placement on the region of interest to monitor stiffness level.

In yet another aspect, a system is described. The system comprises a server. The server comprises a processor, and a memory communicatively coupled to the processor. The processor is operable to receive an image file of a region of interest of an anatomy of a living organism, analyze the image file and extract image coordinates and density information of a plurality of points in the image file, train a neural network using collective information available in a database, register the region of interest of the anatomy as a virtual version using an input from the neural network, and subsequently train the neural network using a user input from a user and the collective information available in the database. The database records the collective information with respect to a plurality of clusters of different physiological states of the living organism.

In an embodiment, the processor is further operable to perform a treatment on the region of interest.

In another embodiment, the system further comprises a surface compliance device.

In yet another embodiment, the surface compliance device comprises a force sensor and a tracking device.

In yet another embodiment, the force sensor is operable to generate closed loop information of the region of interest.

In yet another embodiment, the tracking device is operable to track at least one of a location, and a position of the region of interest where the surface compliance device is in contact with the region of interest.

In yet another embodiment, the surface compliance device comprises a glove.

In yet another embodiment, the force sensor is embedded into a tactile region of the surface compliance device.

In yet another embodiment, the surface compliance device is operable to trace a surface of the region of interest and paint a feature of the region of interest.

In yet another embodiment, the surface compliance device is operable to trace a surface of the region of interest and paint a feature of the region of interest.

In yet another embodiment, the processor is further operable to generate a virtual surgery generated alignment guide based on tracking a three-dimensional physical incarnation and recognizing the first color and the first identifier, and the second color and the second identifier on the three-dimensional physical incarnation.

In yet another embodiment, the processor is further operable to generate a virtual version of the virtual surgery generated alignment guide, wherein the virtual version of the virtual surgery generated alignment guide comprises at least one of a two-dimensional virtual surgery generated alignment guide, and a three-dimensional virtual surgery generated alignment guide.

In yet another aspect, a non-transitory computer storage medium is described. The non-transitory computer storage medium stores a sequence of instructions which when executed causes receiving an image file of a region of interest of an anatomy of a living organism, analyzing the image file and extracting image coordinates and density information of a plurality of points in the image file, training a neural network using collective information available in a database, registering the region of interest of the anatomy as a virtual version using an input from the neural network, and subsequently training the neural network using a user input from a user and the collective information available in the database. The collective information is recorded in the database with respect to a plurality of clusters of different physiological states of the living organism.

In an embodiment, the non-transitory computer storage medium further causes to perform a treatment on the region of interest.

In another embodiment, the non-transitory computer storage medium further causes generating a virtual surgery generated alignment guide based on tracking a three-dimensional physical incarnation and recognizing the first color and the first identifier, and the second color and the second identifier on the three-dimensional physical incarnation.

In yet another embodiment, the non-transitory computer storage medium further causes generating a virtual version of the virtual surgery generated alignment guide, wherein the virtual version of the virtual surgery generated alignment guide comprises at least one of a two-dimensional virtual surgery generated alignment guide, and a three-dimensional virtual surgery generated alignment guide.

In yet another aspect, a method is described herein. The method comprises receiving an image file of a region of interest of an anatomy of a living organism, analyzing the image file and extracting image coordinates and density information of a plurality of points in the image file, training a neural network using collective information available in a database, registering the region of interest of the anatomy as a virtual version using an input from the neural network, and subsequently training the neural network using a user input from a user and the collective information available in the database. The collective information is recorded in the database with respect to a plurality of clusters of different physiological states of the living organism.

In an embodiment, registering the region of interest as the virtual version enables recommending at least one of a treatment procedure, a treatment plan, and a treatment location of the region of interest based on the collective information in the database.

In another embodiment, recommending at least one of the treatment procedure, the treatment plan, and the treatment location of the region of interest based on the collective information in the database comprises: creating the treatment plan to at least one of reach and approach one of an area of interest and an object within the region of interest in six degrees of freedom via a path through at least one of invasive route, and partially invasive route, and recommending the treatment plan to at least one of an automated machine, a semi-automated machine, and a surgeon to perform the treatment.

In yet another embodiment, creating the treatment plan comprises automatically generating the path, by the neural network, that guide one of the automated machine, the semi-automated machine, and the surgeon to at least one of reach and approach one of the area of interest and the object within the region of interest, the path comprises at least one of a straight path, a regular path, a curved path, and an irregular path.

In yet another embodiment, the method further comprises: training the neural network using engineering safety rules and surgeon prescribed rules to generate the path to at least one of reach and approach one of the area of interest and the object within the region of interest.

In yet another embodiment, the method further comprises: creating a virtual surgery generated alignment guide based on tracking a three-dimensional physical incarnation of the region of interest and recognizing a first color and a first identifier, and a second color and a second identifier on the three-dimensional physical incarnation.

In yet another embodiment, the method further comprises: generating a virtual version of the virtual surgery generated alignment guide. The virtual version of the virtual surgery generated alignment guide comprises at least one of a two-dimensional virtual surgery generated alignment guide and a three-dimensional virtual surgery generated alignment guide.

In yet another embodiment, the method further comprises: virtually attaching the virtual version of the virtual surgery generated alignment guide to a physiological feature at a first location in the region of interest where a surgical incision has created enough opening to expose medical image predicted surface on the region of interest.

In yet another embodiment, the method further comprises: analyzing, using the neural network, the virtual attachment of the virtual surgery generated alignment guide on the physiological feature, creating a physical version of the virtual surgery generated alignment guide, and physically attaching the virtual surgery generated alignment guide to the physiological feature at the first location in the region of interest based on the analyzing performed.

In yet another embodiment, the virtual surgery generated alignment guide comprises a coupling feature adapted to couple at least one external attachment with the virtual surgery generated alignment guide mechanically and electronically.

In yet another embodiment, the virtual version of the virtual surgery generated alignment guide appropriately fits the region of interest of the anatomy and enables effective and instant registration of a location and an orientation of the region of interest in relation to a second region of interest of the anatomy.

In yet another embodiment, the method further comprises: measuring the virtual version of the region of interest using a virtual measurement tool, and rendering virtual measurements and a treatment plan of the region of interest. The rendering of the virtual measurements and the treatment plan enables the user to one of mark surgical measurements and make surgical notes prior to the treatment.

In yet another embodiment, creating the virtual surgery generated alignment guide comprises a slot with an anterior protrusion tool to prevent a saw blade from plunging deeper than a length of an anterior protrusion of the region of interest to prevent at least one of soft-tissue damage and artery damage.

In yet another aspect, a system is described herein. The system comprises a server. The server comprises a processor, and a memory communicatively coupled to the processor. The processor is operable to receive an image file of a region of interest of an anatomy of a living organism, analyze the image file and extract image coordinates and density information of a plurality of points in the image file, train a neural network using collective information available in a database, register the region of interest of the anatomy as a virtual version using an input from the neural network, and subsequently train the neural network using a user input from a user and the collective information available in the database. The collective information is recorded in the database with respect to a plurality of clusters of different physiological states of the living organism.

In an embodiment, the system further comprises: a surface compliance device that comprises a force sensor operable to generate closed loop information of the region of interest, and a tracking device operable to track at least one of a location, and a position of the region of interest at which the surface compliance device is in contact with the region of interest.

In another embodiment, the surface compliance device comprises a glove held by the user operable to at least one of trace a surface of the region of interest and paint a feature of the region of interest.

In yet another embodiment, the method further comprises: a virtual surgery generated alignment guide that comprises a first tool, a second tool, and a third tool. The first tool is adapted to identify and match the region of interest in relation to the anatomy. The second tool is adapted to hold and fasten an external instrument. The third tool is adapted to hold and affix an alignment guide.

In yet another embodiment, the virtual surgery generated alignment guide comprises at least one of a printed tracking feature and a detectable wave frequency.

In yet another embodiment, the printed tracking feature comprises one of a tracking code and a quick response (QR) code. The printed tracking feature provides information of at least one of depth, arteries, veins, tissues, ligaments of the region of interest and a tool associated with the virtual surgery generated alignment guide.

In yet another aspect, a non-transitory computer storage medium is described herein. The non-transitory computer storage medium stores a sequence of instructions, which when executed by a processor, causes: receiving an image file of a region of interest of an anatomy of a living organism, analyzing the image file and extracting image coordinates and density information of a plurality of points in the image file, training a neural network using collective information available in a database, registering the region of interest of the anatomy as a virtual version using an input from the neural network, and subsequently training the neural network using a user input from a user and the collective information available in the database. The collective information is recorded in the database with respect to a plurality of clusters of different physiological states of the living organism.

The methods and systems disclosed herein may be implemented in any means for achieving various aspects and may be executed in a form of a non-transitory machine-readable medium embodying a set of instructions that, when executed by a machine, causes the machine to perform any of the operations disclosed herein. Other features will be apparent from the accompanying drawings and from the detailed description that follows.

BRIEF DESCRIPTION OF THE DRAWINGS

The embodiments of this invention are illustrated by way of example and not limitation in the figures of the accompanying drawings, in which like references indicate similar elements and in which.

Figure 1:
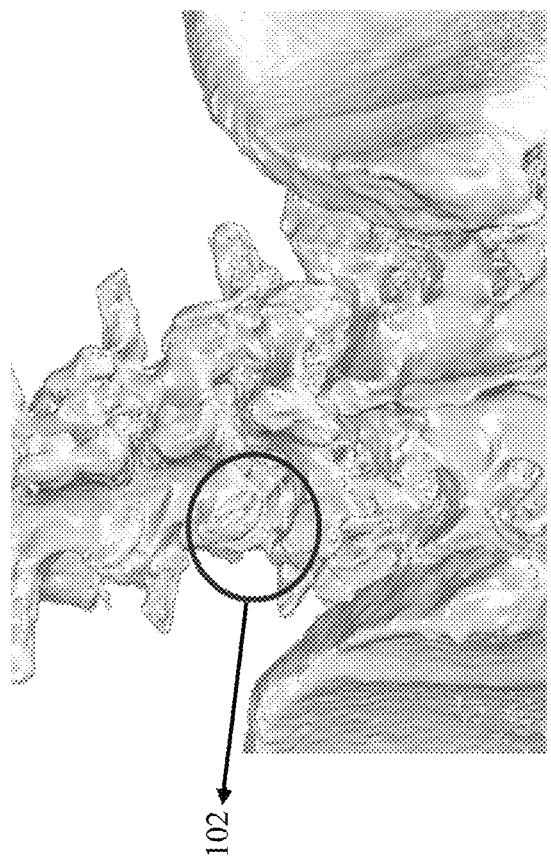
FIG. 1 illustrates a traditional process of segmentation that recognizes a segment of a region of interest of an image as a bone based on a single predefined threshold value, according to a prior art.

Other features of the present embodiments will be apparent from the accompanying drawings and from the detailed description that follows.

DETAILED DESCRIPTION

For simplicity and clarity of illustration, the drawing figures illustrate the general manner of construction. Descriptions and details of well-known features and techniques may be omitted to avoid unnecessarily obscuring the present disclosure. The dimensions of some of the elements in the figures may be exaggerated relative to other elements to help improve understanding of embodiments of the present disclosure. The same reference numeral in different figures denotes the same elements.

Although the following detailed description contains many specifics for the purpose of illustration, a person of ordinary skill in the art will appreciate that many variations and alterations to the following details can be made and are considered to be included herein.

Accordingly, the following embodiments are set forth without any loss of generality to, and without imposing limitations upon, any claims set forth. It is also to be understood that the terminology used herein is for the purpose of describing particular embodiments only and is not intended to be limiting. Unless defined otherwise, all technical and scientific terms used herein have the same meaning as commonly understood by one with ordinary skill in the art to which this disclosure belongs.

The articles "a" and "an" are used herein to refer to one or to more than one (i.e., to at least one) of the grammatical object of the article. By way of example, "an element" means one element or more than one element.

No element act, or instruction used herein should be construed as critical or essential unless explicitly described as such. Furthermore, as used herein, the term "set" is intended to include items (e.g., related items, unrelated items, a combination of related items and unrelated items, etc.), and may be used interchangeably with "one or more." Where only one item is intended, the term "one" or similar language is used. Also, as used herein, the terms "has", "have", "having", or the like are intended to be open-ended terms. Further, the phrase "based on" is intended to mean "based, at least in part, on" unless explicitly stated otherwise.

The terms "first", "second", "third", and the like in the description and in the claims, if any, are used for distinguishing between similar elements and not necessarily for describing a particular sequence or chronological order. It is to be understood that the terms so used are interchangeable under appropriate circumstances such that the embodiments described herein are, for example, capable of operation in sequences other than those illustrated or otherwise described herein. Furthermore, the terms "include", "have", and any variations thereof, are intended to cover a non-exclusive inclusion, such that a process, method, system, article, device, or apparatus that comprises a list of elements is not necessarily limited to those elements but may include other elements not expressly listed or inherent to such process, method, system, article, device, or apparatus.

The terms "left", "right", "front", "back", "top", "bottom", "over", "under", and the like in the description and in the claims, if any, are used for descriptive purposes and not necessarily for describing permanent relative positions. It is to be understood that the terms so used are interchangeable under appropriate circumstances such that the embodiments of the apparatus, methods, and/or articles of manufacture described herein are, for example, capable of operation in other orientations than those illustrated or otherwise described herein.

The terms "couple", "coupled", "couples", "coupling", and the like should be broadly understood and referred to as connecting two or more elements mechanically, electrically, and/or otherwise. Two or more electrical elements may be electrically coupled together, but not be mechanically or otherwise coupled together. Coupling may be for any length of time, e.g., permanent, or semi-permanent or only for an instant. "Electrical coupling" includes electrical coupling of all types. The absence of the word "removably", "removable", and the like near the word "coupled", and the like does not mean that the coupling, etc. in question is or is not removable.

As defined herein, two or more elements or modules are "integral" or "integrated" if they operate functionally together. As defined herein, two or more elements are "non-integral" if each element can operate functionally independently.

The present invention may be embodied in other specific forms without departing from its spirit or characteristics. The described embodiments are to be considered in all respects only as illustrative and not restrictive. The scope of the invention is, therefore, indicated by the appended claims rather than by the foregoing description. All variations which come within the meaning and range of equivalency of the claims are to be embraced within their scope.

As defined herein, "approximately" can mean within a specified or unspecified range of the specified or unspecified stated value. In some embodiments, "approximately" can mean within plus or minus ten percent of the stated value. In other embodiments, "approximately" can mean within plus or minus five percent of the stated value. In further embodiments, "approximately" can mean within plus or minus three percent of the stated value. In yet other embodiments, "approximately" can mean within plus or minus one percent of the stated value.

Implementations and all of the functional operations described in this specification may be realized in digital electronic circuitry, or in computer software, firmware, or hardware, including the structures disclosed in this specification and their structural equivalents, or in combinations of one or more of them. Implementations may be realized as one or more computer program products i.e., one or more modules of computer program instructions encoded on a computer-readable medium for execution by, or to control the operation of, data processing apparatus. The computer-readable medium may be a machine-readable storage device, a machine-readable storage substrate, a memory device, a composition of matter affecting a machine-readable propagated signal, or a combination of one or more of them. The term "computing system" encompasses all apparatus, devices, and machines for processing data, including by way of example, a programmable processor, a computer, or multiple processors or computers. The apparatus may include, in addition to hardware, code that creates an execution environment for the computer program in question, e.g., code that constitutes processor firmware, a protocol stack, a database management system, an operating system, or a combination of one or more of them. A propagated signal is an artificially generated signal (e.g., a machine-generated electrical, optical, or electromagnetic signal) that is generated to encode information for transmission to a suitable receiver apparatus.

The actual specialized control hardware or software code used to implement these systems and/or methods is not limiting of the implementations. It being understood that any software and any hardware, without reference to specific software and hardware, can be designed to implement the operation and behavior of the systems and/or methods described herein A computer program (also known as a program, software, software application, script, or code) may be written in any appropriate form of programming language, including compiled or interpreted languages, and it may be deployed in any appropriate form, including as a standalone program or as a module, component, subroutine, or other unit suitable for use in a computing environment. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

The processes and logic flows described in this specification may be performed by one or more programmable processors executing one or more computer programs to perform functions by operating on input data and generating output. The processes and logic flows may also be performed by, and apparatus may also be implemented as, special purpose logic circuitry, for example, without limitation, a Field Programmable Gate Array (FPGA), an Application Specific Integrated Circuit (ASIC), Application Specific Standard Products (ASSPs), System-On-a-Chip (SOC) systems, Complex Programmable Logic Devices (CPLDs), etc.

Processors suitable for the execution of a computer program include, by way of example, both general and special purpose microprocessors, and any one or more processors of any appropriate kind of digital computer. Generally, a processor will receive instructions and data from a read-only memory or a random-access memory or both. Elements of a computer can include a processor for performing instructions and one or more memory devices for storing instructions and data. Generally, a computer will also include, or be operatively coupled to receive data, transfer data or both, to/from one or more mass storage devices for storing data e.g., magnetic disks, magneto optical disks, optical disks, or solid-state disks. However, a computer need not have such devices. Moreover, a computer may be embedded in another device, e.g., a mobile telephone, a personal digital assistant (PDA), a mobile audio player, a Global Positioning System (GPS) receiver, etc. Computer-readable media suitable for storing computer program instructions and data include all forms of non-volatile memory, media and memory devices, including, by way of example, semiconductor memory devices (e.g., Erasable Programmable Read-Only Memory (EPROM), Electronically Erasable Programmable Read-Only Memory (EEPROM), and flash memory devices), magnetic disks (e.g., internal hard disks or removable disks), magneto optical disks (e.g. Compact Disc Read-Only Memory (CD ROM) disks, Digital Versatile Disk-Read-Only Memory (DVD-ROM) disks) and solid-state disks. The processor and the memory may be supplemented by, or incorporated in, special purpose logic circuitry.

To provide for interaction with a user, implementations may be realized on a computer having a display device, e.g., a Cathode Ray Tube (CRT) or Liquid Crystal Display (LCD) monitor, for displaying information to the user, and a keyboard and a pointing device, e.g., a mouse or a trackball, by which the user may provide input to the computer. Other kinds of devices may be used to provide for interaction with a user as well; for example, feedback provided to the user may be any appropriate form of sensory feedback, e.g., visual feedback, auditory feedback, or tactile feedback; and input from the user may be received in any appropriate form, including acoustic, speech, or tactile input.

Implementations may be realized in a computing system that includes a back-end component, e.g., a data server, or that includes a middleware component, e.g., an application server, or that includes a front-end component, e.g., a client computer having a graphical user interface or a Web browser through which a user may interact with an implementation, or any appropriate combination of one or more such back-end, middleware, or front-end components. The components of the system may be interconnected by any appropriate form or medium of digital data communication, e.g., a communication network. Examples of communication networks include a Local AreaNetwork (LAN) and a Wide AreaNetwork (WAN), e.g., Intranet and Internet.

The computing system may include clients and servers. A client and server are generally remote from each other and typically interact through a communication network. The relationship of the client and server arises by virtue of computer programs running on the respective computers and having a client-server relationship to each other.

Embodiments of the present invention may comprise or utilize a special purpose or general purpose computer including computer hardware. Embodiments within the scope of the present invention may also include physical and other computer-readable media for carrying or storing computer-executable instructions and/or data structures. Such computer-readable media can be any media that can be accessed by a general purpose or special purpose computer system. Computer-readable media that store computer-executable instructions are physical storage media. Computer-readable media that carry computer-executable instructions are transmission media. Thus, by way of example and not limitation, embodiments of the invention can comprise at least two distinctly different kinds of computer-readable media: physical computer-readable storage media and transmission computer-readable media.

Although the present embodiments have been described with reference to specific example embodiments, it will be evident that various modifications and changes may be made to these embodiments without departing from the broader spirit and scope of the various embodiments. For example, the various devices, units, and modules described herein may be enabled and operated using hardware circuitry (e.g., Complementary Metal Oxide Semiconductor (CMOS) based logic circuitry), firmware, software (e.g., embodied in a non-transitory machine-readable medium), or any combination of hardware, firmware, and software. For example, the various electrical structures and methods may be embodied using transistors, logic gates, and electrical circuits (e.g., Application Specific Integrated Circuit (ASIC) and/or Digital Signal Processor (DSP) circuit).

In addition, it will be appreciated that the various operations, processes, and methods disclosed herein may be embodied in a non-transitory machine-readable medium and/or a system. Accordingly, the specification and drawings are to be regarded in an illustrative rather than a restrictive sense.

Physical computer-readable storage media includes RAM, ROM, EEPROM, CD-ROM or other optical disk storage (such as CDs, DVDs, etc.), magnetic disk storage or other magnetic storage devices, solid-state disks or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmission media can include a network and/or data links which can be used to carry desired program code means in the form of computer-executable instructions or data structures, and which can be accessed by a general purpose or special purpose computer. Combinations of the above, that enable the transport of electronic data between computer systems and/or modules and/or other electronic devices, are also included within the scope of computer-readable media.

Further, upon reaching various computer system components, program code means in the form of computer-executable instructions or data structures can be transferred automatically from transmission computer-readable media to physical computer-readable storage media (or vice versa). For example, computer-executable instructions or data structures received over a network or data link can be buffered in RAM within a network interface module (NIC), and then eventually transferred to computer system RAM and/or to less volatile computer-readable physical storage media at a computer system. Thus, computer-readable physical storage media can be included in computer system components that also (or even primarily) utilize transmission media.

Computer-executable instructions comprise, for example, instructions and data which cause a general purpose computer, special purpose computer, or special purpose processing device to perform a certain function or group of functions. The computer-executable instructions may be, for example, binary, intermediate format instructions such as assembly language, or even source code. Although the subject matter has been described in language specific to structural features and/or methodological acts, it is to be understood that the subject matter defined in the claims is not necessarily limited to the described features or acts described. Rather, the described features and acts are disclosed as example forms of implementing the claims.

While this specification contains many specifics, these should not be construed as limitations on the scope of the disclosure or of what may be claimed, but rather as descriptions of features specific to particular implementations. Certain features that are described in this specification in the context of separate implementations may also be implemented in combination in a single implementation. Conversely, various features that are described in the context of a single implementation may also be implemented in multiple implementations separately or in any suitable sub-combination. Moreover, although features may be described as acting in certain combinations and even initially claimed as such, one or more features from a claimed combination may in some cases be excised from the combination, and the claimed combination may be directed to a sub-combination or variation of a sub-combination.

Similarly, while operations are depicted in the drawings in a particular order to achieve desired results, this should not be understood as requiring that such operations be performed in the particular order shown or in sequential order or that all illustrated operations be performed, to achieve desirable results. In certain circumstances, multitasking and parallel processing may be advantageous. Moreover, the separation of various system components in the implementations should not be understood as requiring such separation in all implementations, and it should be understood that the described program components and systems may generally be integrated together in a single software product or packaged into multiple software products.

As used herein, the term component is intended to be broadly construed as hardware, firmware, and/or a combination of hardware and software.

The computing system may include clients and servers. A client and server are generally remote from each other and typically interact through a communication network. The relationship of client and server arises by virtue of computer programs running on the respective computers and having a client-server relationship to each other.

Computer-executable instructions comprise, for example, instructions and data which cause a general-purpose computer, special purpose computer, or special purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described. Rather, the described features and acts are disclosed as example forms of implementing the claims.

Even though particular combinations of features are recited in the claims and/or disclosed in the specification, these combinations are not intended to limit the disclosure of possible implementations. Other implementations are within the scope of the following claims. For example, the actions recited in the claims may be performed in a different order and still achieve desirable results. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

Further, the methods may be practiced by a computer system including one or more processors and computer-readable media such as computer memory. In particular, the computer memory may store computer-executable instructions that when executed by one or more processors cause various functions to be performed such as the acts recited in the embodiments.

The disclosure provides illustration and description but is not intended to be exhaustive or to limit the implementations to the precise form disclosed. Modifications and variations are possible in light of the above disclosure or may be acquired from practice of the implementations.

Those skilled in the art will appreciate that the invention may be practiced in network computing environments with many types of computer system configurations including personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, etc. The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

In order to fully understand the scope of the invention, the following terms used herein are hereby defined.

The term "comprising", which is synonymous with "including", "containing", or "characterized by" here is defined as being inclusive or open-ended, and does not exclude additional, unrecited elements or method steps, unless the context clearly requires otherwise.

The term "device" is defined as an electronic element, or a machine adapted for a particular purpose.

The term "user" as used herein refers to a surgeon, a medical practitioner, a physician, a caretaker, a doctor, an automated machine, and a semi-automated machine.

The term "server" is defined as a computer that manages network resources.

The term "communicatively coupled" is defined as devices connected in a way that permits communication.

The term "configured" is defined as arranged within the system to perform certain functions.

The term "receiving" is defined as being given information.

The term "region of interest" as used herein refers to a subset of an image or a dataset identified for a particular purpose. The region of interest may refer to a portion in an anatomy.

The term "image" as used herein refers to a representation of an internal and/or external form of a living organism.

The term "image file" as used herein refers to a file that comprises graphics data.

The term "cluster" as used herein refers to a group of physiological states of the living organism.

The term "sub cluster" as used herein refers to a subset of the cluster.

The term "living organism" as used herein refers to an organism that shows characteristics of being alive.

The term "anatomy" as used herein refers to structure and internal workings of the living organism.

The term "collective information" as used herein refers to whole information available in a database at that instant.

The term "outcome" as used herein refers to a consequence or result of a treatment performed on the region of interest.

The term "patient reported outcome measures (PROMs)" refers to quality measures derived from outcomes reported by patients. Patient-reported outcome measures (PROMs) capture a person's perception of their own health through questionnaires. Responses to PROMs questions help hospitals and healthcare services provide the care that patients need and want.

The term "based on" is defined as dependent on.

The term "a plurality of" is defined as multiple.

The term "memory" is defined as any device in which information can be stored.

The term "execute" is defined as run or launch.

The term "instructions" is defined as software program or machine executable code.

The term "neural network" as used herein refers to a computational learning system that uses a network of functions to understand and translate a data input of one form into a desired output, usually in another form.

The term "pretraining" as used herein refers to a training provided to a neural network prior to starting a particular task.

The term "virtual action" as used herein refers to an action that is performed within a virtual environment.

The term "treatment" as used herein refers to a medical care given to the living organism. The treatment also refers to a use of an agent, procedure, or a regimen, such as a drug or surgery, or exercise, in an attempt to cure or mitigate a disease, condition, injury or illness.

The term "physiological state" as used herein refers to a condition or state of a body or a bodily function of the living organism. The physiological state may be one among a plurality of healthy cluster states or one among a plurality of unhealthy cluster states.

The term "point cloud" as used herein refers to a collection of data points defined by a given coordinates system. The point cloud is a bunch of points that are connected or related to each other.

The term "coordinates" as used herein refers to a set of values that show an exact position.

The term "outlining" as used herein refers to marking a boundary of the region of interest.

The term "component" is intended to be broadly construed as hardware, firmware, and/or a combination of hardware and software.

The term "foreign object" as used herein refers to an object/thing that is present in a body but does not belong to the body.

The term "threshold" as used herein refers to a limit that must be exceeded for a certain reaction, phenomenon, result, or condition to occur.

The term"labeling" as used herein refers to describing someone or something in a word or short phase.

The term "segmenting" as used herein refers to a division of the region of interest into segments.

The term "landmarks" as used herein refers to locations on a bone that is accepted to be a reproducible feature, and also ligament attachments and tendon attachments that are relevant for kinematics.

The term "processor" is defined as a component for executing instructions stored in memory. The processor may be within the server or outside the server.

The term "transceivers" is defined as a component used for both transmission and reception of digital data.

The term "pre-stored information" as used herein refers to the information that is stored in advance in a database of being needed to do a particular task.

The term "ADL" as used herein refers to activity of daily living i.e., a task of everyday life.

The term "kinematics" as used herein refers to aspects of motion of the body of the living organism.

The term "incarnation" as used herein refers to a physical form of the region of interest. The incarnation is made up of any metal and/or any material.

The term "surface compliance device" as used herein refers to a device adapted to trace a surface of the region of interest and register a virtual version of the region of interest. The surface compliance device is adapted to register the virtual version of the region of interest without any intruding rays onto the region of interest. The surface compliance device eliminates a need for medical imaging such as a computed tomography (CT) scan, a magnetic resonance imaging (MRI) scan and the like.

The term "virtual surgery generated alignment guide" as used herein refers to an alignment guide that can be affixed to the region of interest. The alignment guide is affixed exactly to an optimum location of the region of interest in only one way thereby reducing medical error. The alignment guide is also capable of rendering virtual measurements and surgery notes, as and when scanned by the surgeon. The alignment guide further depicts cut planes, density information, ligament tensions and the like onto the region of interest. The information rendered by the alignment guide assists the surgeon during the treatment.

The term "database" refers to a collection of information that is organized so that it can be easily accessed, managed, and updated. Computer databases typically contain aggregations of data records or files.

The term "Sensor" is a device that measures physical input from its environment and converts it into data that can be interpreted by either a human or a machine. Most sensors are electronic (the data is converted into electronic data), but some are simpler, such as a glass thermometer, which presents visual data.

Example embodiments, as described below, may be used to provide patient specific treatment planning. It will be appreciated that the various embodiments discussed herein need not necessarily belong to the same group of embodiments and may be grouped into various other embodiments not explicitly disclosed herein. In the following description, for purposes of explanation, numerous specific details are set forth in order to provide a thorough understanding of the various embodiments.

In an aspect, the present disclosure discloses patient specific treatment planning. An image file of a region of interest of an anatomy is received. The anatomy comprises a bodily structure of a living organism. The image file may comprise a video file. Coordinates information and density information of a plurality of points of an image of the image file are extracted. A neural network is pretrained based on the coordinates information, the density information and collective information available in a database. A virtual action and/or a treatment on the region of interest is performed, via a user, based on the collective information in the database. The neural network is further trained based on at least one of a user input, and the collective information from the database. The patient specific treatment planning finds application in at least one of but not limited to a sports medicine, a trauma, an orthopedics, etc.

Figure 2:
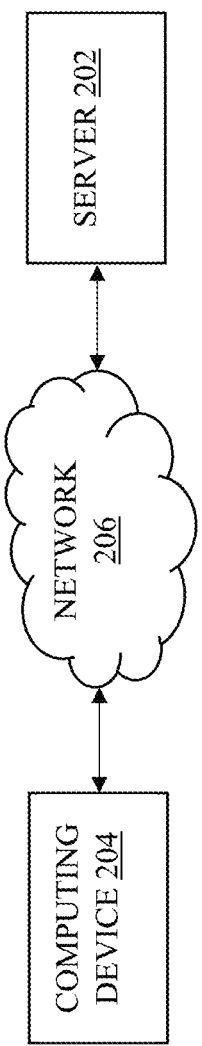
FIG. 2 illustrates a view of a system, according to one or more embodiments.

FIG. 2 illustrates a view of a system, according to one or more embodiments. The system assists in providing treatment to a patient and pre-treatment and post-treatment recovery tracking. The system comprises a computing device 204, a server 202, and a network 206. The computing device 204 may be a device associated with a user. The computing device 204 comprises at least one of a computer, a laptop, a personal computer, a smartphone, a tablet, and the like. The server 202 may be one of a remote server (e.g., a cloud server) and a physical server. The server 202 is configured to provide services to the computing device 204. The server 202 is communicatively coupled to the computing device 204 via a network 206. The network 206 may be a wireless network and a wired network.

The system may comprise a surface compliance device. The surface compliance device may also be communicatively coupled to the server 202. The surface compliance device may be a glove worn by the user or a robot. The surface compliance device is configured to trace a surface of the region of interest and register landmarks of the region of interest. The surface compliance device is adapted to register a virtual version of the region of interest without any intruding rays. The surface compliance device utilized herein eliminates a need for medical imaging techniques such as a computed tomography (CT) scan and a magnetic resonance imaging (MRI) scan.

The server described herein is configured to automatically generate a virtual surgery generated alignment guide. The server generates the virtual surgery generated alignment guide by analyzing at least one of image file, and density point clouds of the region of interest. The server is configured to generate the virtual surgery generated alignment guide specific to the region of interest. In an embodiment, the server creates a virtual version of the virtual surgery generated alignment guide. The server is also configured to analyze matching of the virtual surgery generated alignment guide onto the region of interest. The server creates a three-dimensional virtual protype of the virtual surgery generated alignment guide. The three-dimensional virtual protype of the virtual surgery generated alignment guide is utilized to create the three-dimensional physical incarnation of the virtual surgery generated alignment guide.

Figure 3:
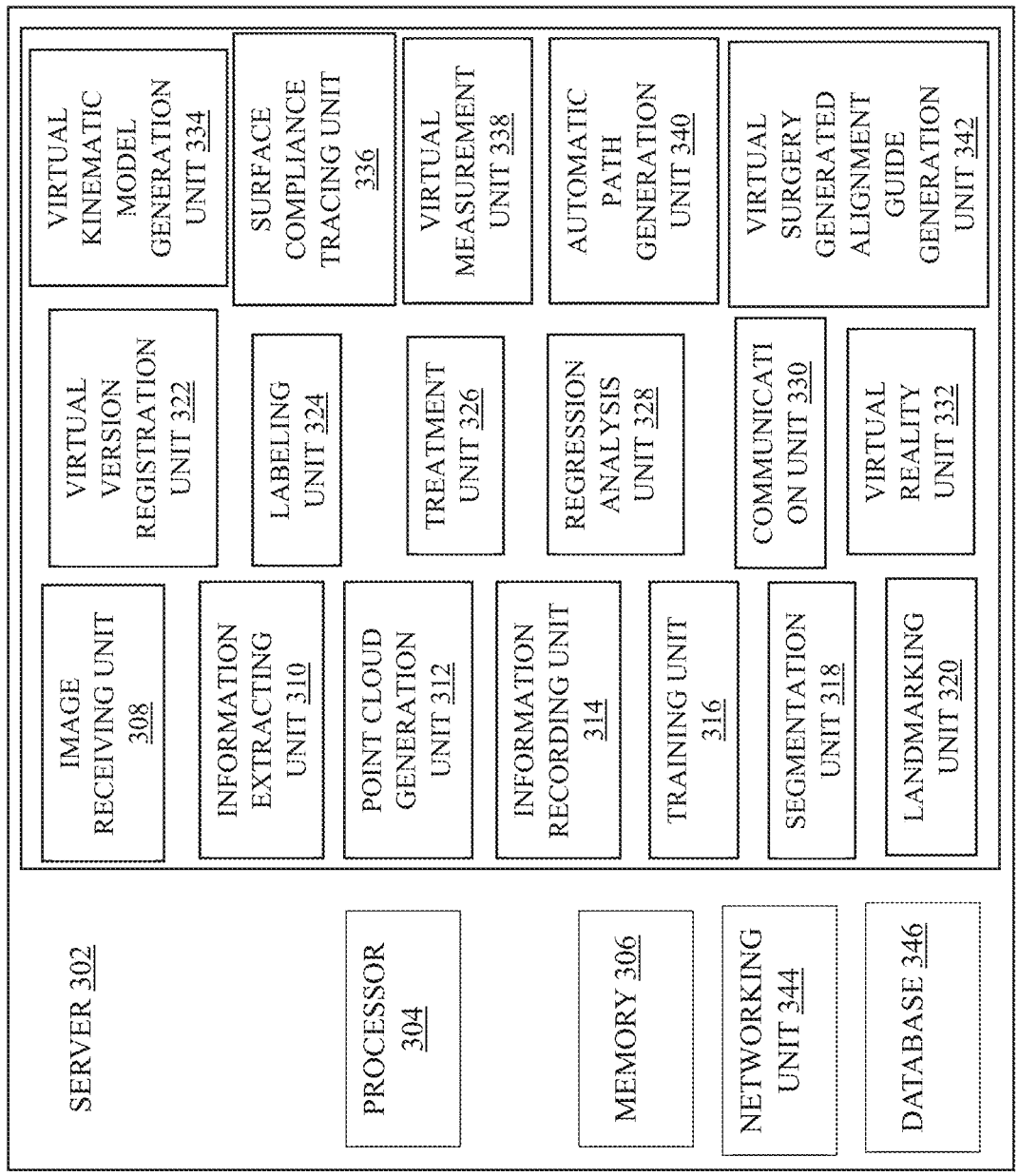
FIG. 3 illustrates an exploded view of a server, according to one or more embodiments.

FIG. 3 illustrates an exploded view of a server 302, according to one or more embodiments. The server 302 disclosed herein comprises a memory 306 and a processor 304. The processor 304 is communicatively coupled to the memory 306. The processor 304 may take a form of a single core processor, multi-core processor (e.g., a dual core processor, triple core processor, quad core processor, etc.), microprocessor, etc. In some embodiments, the processor 304 may be external to an apparatus (e.g., server). For example, the processor 304 may be a remote processor (e.g., a cloud-based processor). Alternatively, or additionally, the processor 304 may be internal and/or local to the apparatus. The server 302 further comprises an image receiving unit 208, an information extracting unit 310, a point cloud generation unit 312, an information recording unit 314, a training unit 316, a segmentation unit 318, a landmarking unit 320, a virtual version registration unit 322, a labeling unit 324, a treatment unit 326, a regression analysis unit 328, a communication unit 330, a virtual reality unit 332, a virtual kinematic model generation unit 334, a surface compliance tracing unit 336, a virtual measurement unit 338, an automatic path generation unit 340, and a virtual surgery generated alignment guide generation unit 342.

The above-mentioned units in association with the processor is configured to perform patient specific treatment planning. The image receiving unit 208 receives an image file and/or a video file of a region of interest of an anatomy. The anatomy comprises a bodily structure of a living organism. The region of interest may be any part and/or any portion (e.g., a skull, a shoulder, a spine, a knee, a foot, etc.) of the living organism. The anatomy belongs to the living organism. In an embodiment the living organism comprises one of an animal, a human being, a bird, and a mammal. The image file comprises an image and/or a video of the region of interest. The image file comprises one of a Digital Imaging and Communications in Medicine (DICOM) format file, a computed tomography (CT) image file and a magnetic resonance imaging (MRI) format file. In an embodiment, the image file may comprise the video file.

The image receiving unit 308 receives the image file from an image source. The image comprises a plurality of points (e.g., a plurality of pixels, a plurality of voxels, etc.). The image comprises one of a two-dimensional image and a three-dimensional image. In an embodiment, size of the plurality of points comprises one of three by three millimeter cubes and one by one millimeter cubes. In another embodiment, the size of the plurality of points of the image file ranges from 3*3*3 mm cubes to 0.6*0.6*0.6 mm cubes that represents voxels of information and/or pixels of information. In an embodiment, the voxels of information and/or the pixels of information comprise density information. The information extracting unit 310 extracts coordinates information and the density information of each point of the plurality of points of the image. The point cloud generation unit 312 generates point cloud information of the region of interest of the anatomy based on the coordinates information, and the density information. In an embodiment, the point cloud generation unit 312 generates a heat map of the region of interest based on the point cloud information. The heat map distinguishes between a segment of the region of interest with distinct colors.

The information recording unit 314 records the coordinates information and the density information on a database under a plurality of clusters of different physiological states. The database comprises pre-stored information. The pre-stored information comprises a predefined virtual kinematic model, a predefined treatment location, a predefined treatment procedure, a predefined treatment plan, gait data, force data, and predefined density information with respect to each cluster of the plurality of clusters of different physiological states. The plurality of clusters of different physiological states comprises a first cluster (e.g., a healthy cluster state), a second cluster (e.g., an unhealthy cluster state), a third cluster (e.g., an existing cluster state), etc. The plurality of clusters of different physiological states further comprises a fourth cluster based on landmarks of the region of interest, a fifth cluster based on a tendon attachment point and a sixth cluster based on a ligament attachment point of the region of interest.

The training unit 316 pretrains a neural network based on the coordinates information, the density information, and collective information of the database. In an embodiment, the neural network is a convolutional neural network. The segmentation unit 318 segments (e.g., divides, splits) the segment of the region of interest. The segment may comprise a first segment (e.g., a first bone), a second segment (e.g., a second bone), a third segment (e.g., a foreign object), etc. In an embodiment, the first bone comprises a dense bone, the second bone comprises a soft bone and the foreign object comprises a metal object. In another embodiment, the first bone comprises a first bone section comprising a first gradient density, a second bone section comprising a second gradient density, etc. The training unit 316 pretrains the neural network to readily distinguish and locate the first bone section, the second bone section, etc. within the first bone, based on the first gradient density, the second gradient density, etc., respectively. The segmentation unit 318 estimates Hounsfield units of the segment of the region of interest. The segmentation unit 318 further assigns a first threshold value, a second threshold value and a third threshold value to the first segment, the second segment and the third segment, respectively. For example, the first threshold value ranges from 0 to 20% for the first segment (e.g., cancellous bone), the second threshold value ranges from 20% to 80% for the second segment (e.g., cortical bone) and the third threshold value ranges over two thousand Hounsfield units for the third segment (e.g., the foreign object). In an embodiment, percentage values vary for the first segment, the second segment, and the third segment varies and joint types of the first segment, the second segment, and the third segment of each patient of different populations.

The segmentation unit 318 further outlines the first segment, the second segment and the third segment based on the Hounsfield units and marks boundaries associated with the first segment, the second segment and the third segment. For an instance, when the Hounsfield units estimated from the image file ranges from −1024 to 3000 or more, the threshold value is 2500 Hounsfield units or higher for the third segment (e.g., the foreign object) and the highest percentage value assigned is 100%. The Hounsfield units −1024 range corresponds to air. In an embodiment, the training unit 316 trains the neural network with different threshold values for the third segment (e.g., the foreign objects) made of different metals to automatically identify and locate the first segment, the second segment and the third segment. The segmentation unit 318 further determines at least one of an edge and a tunnel between and/or within the segment of the region of interest and determines whether the segment is one segment or two segments. The segmentation unit 318 determines a first density value of a plurality of first points and a second density value of a plurality of second points of the plurality of points in the image file. The plurality of second points is located on either side of the plurality of first points. The segmentation unit 318 determines the plurality of first points as the edge and/or the tunnel, when the plurality of first points comprising the first density value lower than the second density value of the plurality of second points. In an embodiment, the first density value of the plurality of first points is lower than one of 0% to 20% and 20% to 80% of the second density value of the plurality of second points. In another embodiment, the segmentation unit 318 segments sub-segments within the segment. For an example, the segmentation unit 318 segments the region of interest and detects whether the region of interest comprises one bone or two bones within the segment of the region of interest.

The landmarking unit 320 landmarks the segment of the region of interest based on kinematics associated with the segment of the region of interest. The landmarking unit 320 identifies the first cluster (e.g., the healthy cluster state) of the plurality of clusters of different physiological states to which the region of interest belongs. In an embodiment, the cluster (e.g., the first cluster) to which the region of interest belongs is identified using k-nearest neighbor (KNN) analysis. The landmarking unit 320 correlates a virtual kinematic model of the region of interest with the predefined virtual kinematic model of the first cluster. In an embodiment, the first cluster (e.g., the healthy cluster state) comprises multiple clusters based on at least one of the landmarks, the ligament attachment point, the tendon attachment point, and the virtual kinematic models with respect to activity of daily livings (ADLs). The landmarking unit 320 analyzes the kinematics (e.g., motion) associated with the virtual kinematic model and predicts a constraint and a constraint location for the virtual kinematic model. The landmarking unit 320 further determines a first position and a first angle for at least one of the ligament attachment point and the tendon attachment point in the virtual kinematic model at a first level to create/restore an optimum kinematics in the virtual kinematic model. The landmarking unit 320 further determines a second position and a second angle for at least one of the ligament attachment point and the tendon attachment point in the virtual kinematic model at a second level to create/restore the optimum kinematics in the virtual kinematic model, when the first position and the first angle fails to create/restore the optimum kinematics.

The virtual version registration unit 322 creates a virtual version of the region of interest. The virtual version registration unit 322 creates the virtual version as soon as the region of interest is segmented and landmarked. The virtual version registration unit 322 creates the virtual version of the region of interest in at least one of a two-dimensional format and a three-dimensional format. The virtual version registration unit 322 creates the virtual version of the region of interest in six degrees of freedom. The virtual version created can be used to split a portion of the region of interest and analyze interior portions of the region of interest. The virtual version created can be further used to analyze functioning and kinematics of the region of interest.

The labeling unit 324 labels the segment of the region of interest once the segment of the region is landmarked and segmented. The labeling unit 324 labels the segment of the region of interest from one of left to right, right to left, top to bottom and bottom to top. For a first instance, the labeling unit 324 labels the segment of the region of interest from top to bottom, in which a skull is labelled as Z and a foot is labelled as –Z. For a second instance, the labeling unit 324 labels a left knee as +X and a right knee as –X. In an embodiment, the labelling unit 324 enables the user to readily identify and distinguish between the segments of the region of interest. In another embodiment, the labelling unit 324 enables to verify accuracy of the labeling performed on the region of interest and correct the labelling when the accuracy is below a predefined accuracy.

The treatment unit 326 creates a treatment plan for the region of interest. The treatment unit 326 analyzes a defect on the region of interest. The treatment unit 326 simulates the virtual kinematic model of the region of interest and identifies the first cluster from the plurality of clusters of different physiological states to which the region of interest belongs. The treatment unit 326 correlates the virtual kinematic model with the predefined virtual kinematic model of the first cluster. The treatment unit 326 analyzes the kinematics (e.g., motion) associated with the virtual kinematic model of the region of interest and predicts the constraint and the constraint location for the region for the virtual kinematic model to restore the optimum kinematics in the virtual kinematic model of the region of interest. In an embodiment, the treatment unit 326 restores the optimum kinematics by creating virtual points to position/place flexions, extension, attachments, etc. on the region of interest. The treatment unit 326 creates the treatment plan that optimizes the kinematics, a treatment location, etc.

The treatment unit 326 then creates the treatment plan relevant to a cluster (e.g., the first cluster, the second cluster, the third cluster, etc.) of the plurality of clusters of different physiological states to which the region of interest belongs. In an embodiment, the treatment unit 326 then creates the treatment plan to the region of interest based on the kinematics, force data, gait data, etc. associated with the healthy cluster state relevant to the region of interest available in the database at that instant. In an embodiment, the treatment unit 326 creates a first set of rules for the first cluster to which the region of interest belongs. In another embodiment, the first set of rules can be imposed on the region of interest to recover the region of interest. In another embodiment, the treatment unit 326 creates the set of rules for each cluster of the plurality of clusters of different physiological states. In another embodiment, the treatment unit 326 enables the user to register and perform a treatment on the region of interest. The treatment plan comprises a treatment type, a treatment procedure, the ligament attachment point, and the tendon attachment point of the region of interest. In an embodiment, the treatment unit 326 creates the treatment plan to recover the kinematics and retain an activity of daily living of the living organism. The activity of daily living comprise sitting, standing, walking, running, etc. In another embodiment, the treatment unit 326 recovers the kinematics with a compensation factor and estimates a return score to one of the first cluster, the second cluster, the third cluster, etc. In yet another embodiment, the treatment unit 326 retains the activity of daily living back to one of the first cluster (e.g., the healthy cluster state), the second cluster (e.g., the unhealthy cluster state), the third cluster (e.g., the existing cluster state), etc. In yet another embodiment, the treatment unit 326 enables the user to interact with the region of interest on the fly (i.e., during the treatment) and plan the treatment (e.g., orienting an implant at an optimal position, an optimal angle, etc.).

The regression analysis unit 328 performs a regression analysis to perform a cluster correction (i.e., converting the region of interest from one cluster to another cluster). In an embodiment, the regression analysis unit 328 finds the first cluster (e.g., the healthy cluster state) equivalent to the region of interest to analyze the kinematics associated with the healthy cluster state and impose the kinematics on the region of interest. In another embodiment, the regression analysis unit 328 determines at least one parameter from the region of interest that are intended to identify that the region of interest belongs to the first cluster of the plurality of clusters of different physiological states. The information recording unit 314 records first information and second information on the database, in addition to the pre-stored information under the plurality of clusters of different physiological states. The information recording unit 314 records the first information based on a virtual action and the treatment performed on the region of interest. The first information comprises remarks information indicating an outcome of the treatment. The outcome of the treatment comprises a first outcome (e.g., good outcome), a second outcome (e.g., bad outcome), etc. The remarks information further comprises a plurality of first parameters and a plurality of second parameters that contributes to the first outcome and the second outcome, respectively. The plurality of first parameters may comprise first physics assumptions and the plurality of second parameters may comprise second physics assumptions. The information recording unit 314 records the second information based on at least one of the outcome of the treatment and a feedback received from a user. In an embodiment, the user comprises at least one of a surgeon, a physician, a caretaker, a medical practitioner, and a machine. The machine comprises at least one of a semi-automated machine, and an automated machine.

The information recording unit 314 updates the first information on the database based on at least one of the outcome of the treatment and the feedback received from the user. The first information updated comprises a plurality of third parameters and a plurality of fourth parameters that contributes to the first outcome and the second outcome, respectively. In an embodiment, the plurality of third parameters comprises parameters less than or equal to the plurality of first parameters and the plurality of fourth parameters comprises parameters less than or equal to the plurality of second parameters. The virtual action comprises at least one of segmentation, landmarking, labeling, and creating a treatment plan on the region of interest. The virtual action further comprises recommending at least one of a treatment procedure, the treatment plan, and a treatment location of the region of interest based on the collective information in the database. The recommendation of the treatment plan comprises creating the treatment plan to at least one of reach and approach one of an area of interest and an object within the region of interest in six degrees of freedom with a variable path through at least one of invasive route, and partially invasive route, and recommending the treatment plan to at least one of an automated machine, a semi-automated machine, and a surgeon to perform the treatment. In an embodiment, the treatment plan may be created by automatically generating a path, by the neural network. The path may guide one of the automated machine, the semi-automated machine, and the surgeon to at least one of reach and approach one of the area of interest and the object within the region of interest. The path comprises at least one of a straight path, a regular path, a curved path, and an irregular path. The path is generated in compliance to engineering safety rules and surgeon prescribed rules.

The database comprises the collective information. The collective information comprises the pre-stored information, the first information and the second information. The training unit 316 then trains the neural network based on at least one of a user input and the collective information on the database. The user input is received while performing the virtual action and the treatment on the region of interest. In an embodiment, the training unit 316 trains the neural network to a threshold point and/or limit and records the collective information on the database where the sever 302 can function independently without getting an input from the neural network to provide an output to the user. In yet another embodiment, the training unit 316 trains the neural network using the engineering safety rules and the surgeon prescribed rules to generate the path to at least one of reach and approach one of the area of interest and the object within the region of interest.

The information recording unit 314 categorizes and records the collective information under the plurality of clusters of different physiological states. In an embodiment, the information recording unit 314 categorizes and records information associated with the region of interest under a new cluster when the region of interest does not belong to the plurality of clusters of different physiological states. In another embodiment, the information recording unit 314 records the information associated with the region of interest under the plurality of clusters of different physiological states based on at least one of the ligament attachment point, the tendon attachment point, and the landmarks of the region of interest. The plurality of clusters of different physiological states further comprises the fourth cluster (e.g., a cluster based on the landmarks of the region of interest), the fifth cluster (e.g., a cluster based on the tendon attachment point), the sixth cluster (e.g., a cluster based on the ligament attachment point), etc. In yet another embodiment, the information recording unit 314 records the information associated with the region of interest under a plurality of sub-clusters of the plurality of clusters of different physiological states. In yet another embodiment, the information recording unit 314 records the engineering safety rules and the surgeon prescribed rules into the database with respect to the region of interest under respective cluster of the plurality of clusters of different physiological states. The information recording unit 314 also updates the engineering safety rules and the surgeon prescribed rules into the database when there is change in the engineering safety rules and the surgeon prescribed rules.

The communication unit 330 communicates the collective information, and one of a processed image output and a processed video output to a device associated with the server. In an embodiment, the communication unit 330 communicates wirelessly the collective information, and one of the processed image output and the processed video output to the device associated with the server 302. In another embodiment, the communication unit 330 communicates the collective information, and one of the processed image output and the processed video output to the device associated with the server 302, through a wired network. The virtual reality unit 332 provides the processed image output and the processed video output in least one of a virtual reality and an augmented reality enables the user to perform the virtual action and the treatment on the region of interest through at least one of the virtual reality and the augmented reality.

The virtual kinematic model generation unit 334 generates at least one of the virtual kinematic model and a processed image file of the region of interest based on one of the coordinates information, the density information, and the collective information of the database. The virtual kinematic model comprises a three-dimensional virtual kinematic model. The virtual kinematic model generation unit 334 simulates the virtual kinematic model. The virtual kinematic model generation unit 334 virtually displays the functioning of the region of interest and assists the user to perform the treatment on the region of interest. In an embodiment, the virtual kinematic model generation unit 334 assists the user to perform the treatment by depicting the treatment plan (e.g., the treatment procedure) on the region of interest.

The treatment procedure depicted on the region of interest comprises at least one of displaying a boundary on the region of interest, indicating a virtual cut on the region of interest, indicating a position of screws on the region of interest, etc. The virtual kinematic model generation unit 334 displays the boundary on the region of interest and guides the user not to perform an intervention within the boundary during the region of interest. The virtual kinematic model generation unit 334 further indicates a first feature (e.g., the first segment), a second feature (e.g., the second segment), a third feature (e.g., the foreign object) etc. in the virtual kinematic model with the first color and the first identifier, the second color and the second identifier, and the third color and the third identifier etc. respectively. In an embodiment, the virtual kinematic model generation unit 334 further indicates the first feature (e.g. the first segment), the second feature (e.g., the second segment), the third feature (e.g. the foreign object) etc. in the virtual kinematic model with the first color and the first identifier, the second color and the second identifier, and the third color and the third identifier etc. respectively to track a location of a dense bone and depict at least one of a potential implant position, a screw position and a plate position with respect to optimum fixation.

The virtual kinematic model generation unit 334 further enables the machine to print a three-dimensional (3D) physical incarnation of at least one of the processed image file and the virtual kinematic model of the region of interest. The three-dimensional (3D) physical incarnation comprises a physical prototype of the region of interest (e.g., bones). The physical prototype of the region of interest enables the user to view and analyze functioning (e.g., the kinematics) of the three-dimensional physical incarnation. In an embodiment, the virtual kinematic model generation unit 334 further enables the machine to print the three-dimensional (3D) physical incarnation comprising the first feature, the second feature and the third feature with the first color and the first identifier, the second color and the second identifier, and the third color and the third identifier, respectively. In another embodiment, the virtual kinematic model generation unit 334 further positions the three-dimensional physical incarnation, performs one of a two-dimensional (2D) spot-check and diagnosis X-rays to check orientation in surgery, and to check one of a pre-op X-ray, a post-op X-ray and 2D image for extracting three-dimensional physical incarnation information. In yet another embodiment, the virtual kinematic model generation unit 334 further enables the machine to track the three-dimensional (3D) physical incarnation and recognize the first color and the first identifier, the second color and the second identifier, and the third color and the third identifier, etc. In yet another embodiment, the virtual kinematic model generation unit 334 further enables the machine to mimic a tool held by the user and perform the treatment remotely as directed by the user. In yet another embodiment, the virtual kinematic model generation unit 334 enables the user to turn-on and turn-off individual layers of the segment to identify location of various categories of body parts, make decisions and create the treatment plan.

The surface compliance tracing unit 336 is communicatively coupled to a surface compliance device. The surface compliance tracing unit 336 receives closed loop information from the surface compliance device. The closed loop information comprises variable load information from the surgeon while tracing the surface of the region of interest. The variable load information comprises variable load provided by the surgeon at various places of the region of interest. The surface compliance tracing unit 336 recognizes a first load (e.g., first amount of force) among the variable load provided by the surgeon as a first interaction (e.g., a landmark). The surface compliance tracing unit 336 recognizes a second load (e.g., second amount of force) among the variable load provided by the surgeon as a second interaction (e.g., a soft tissue). The surface compliance tracing unit 336 recognizes a third load (e.g., third amount of force) among the variable load provided by the surgeon as a third interaction (e.g., a rigid object). In an embodiment, the surface compliance tracing unit 336 is also configured to determine virtual measurements of the region of interest. The surface compliance tracing unit 336 may determine the virtual measurements by registering various parts (e.g., soft tissue, artery, rigid object, bone, foreign object, ligaments, space between the bones, etc.) of the region of interest.

The virtual measurement unit 338 determines the virtual measurements of the region of interest. The virtual measurement unit 338 determines the virtual measurements by analyzing the virtual version of the region of interest. In an embodiment, the virtual measurement unit 338 may determine the virtual measurements using a virtual measurement tool. The virtual measurements comprise in-depth measurements, inner diameter, length, breadth, and height of the region of interest. The virtual measurements assist the user (e.g., surgeon) to perform a manual surgery where one of a robotic and an automated surgery is used. The virtual measurement unit 338 renders the virtual measurements such as cut planes, anterior protrusion length, etc. at an exact location of the region of interest. The virtual measurements may assist the surgeon during the treatment. The virtual measurements enable the surgeon to at least one of mark surgical instruments and make surgical notes prior to the treatment. The virtual measurement unit 338 also determines an anterior protrusion length to be drilled onto the region of interest. The anterior protrusion length is determined to drill without damaging any artery or soft tissue.

The automatic path generation unit 340 automatically generates a path to reach an area of interest within the region of interest. The automatic path generation unit 340 enables the user to select at least one of the area of interest and an object. The automatic path generation unit 340 then generates the path to at least one of the area of interest and the object. In an embodiment, the automatic path generation unit 340 automatically generates more than path to the area of interest. The automatic path generation unit 340 may recommend the path among the paths generated. The automatic path generation unit 340 recommends the path based on at least one of a type of treatment and an instrument to be utilized in treatment. In an embodiment, the automatic path generation unit 340 also receive inputs from the user such as the type of the treatment, and the instrument. In another embodiment, the automatic path generation unit 238 extracts the type of the treatment, and the instrument to be used for the treatment from the database.

The virtual surgery alignment guide generation unit 342 generates a virtual surgery generated alignment guide using the virtual version of the region of interest. The virtual surgery alignment guide fits exactly the region of interest at an appropriate location. The virtual surgery alignment guide fits the region of interest in only one way such that there is no medical error. The virtual surgery generated alignment guide comprises a first portion, and a second portion. The first portion refers to a portion that gets affixed to the region of interest. The first portion is adapted to attach the virtual surgery generated alignment guide exactly to an optimum region on the region of interest. Further the first portion is adapted to exactly align the virtual surgery generated alignment guide with respect to the region of interest. The second portion is adapted to hold one or more tools that may assist the surgeon during the treatment.

The virtual surgery generated alignment guide comprises at least one of a printed tracking feature and detectable wave frequency. The printed tracking feature comprises a colored quick response (QR) code. The printed tracking feature may also be any tracking code. The printed tracking feature renders the information when scanned through a camera or a scanning device. The printed tracking feature and the detectable wave frequency may assist the surgeon while performing the treatment.

The server 302 further comprises a networking module 344, and a database 346. The networking module 344 is configured to communicate with the computing device, the database 346, and any external instruments communicatively coupled to the server 302. The database 346 may be a remote database or a physical database associate within the server 302.

Figure 4:
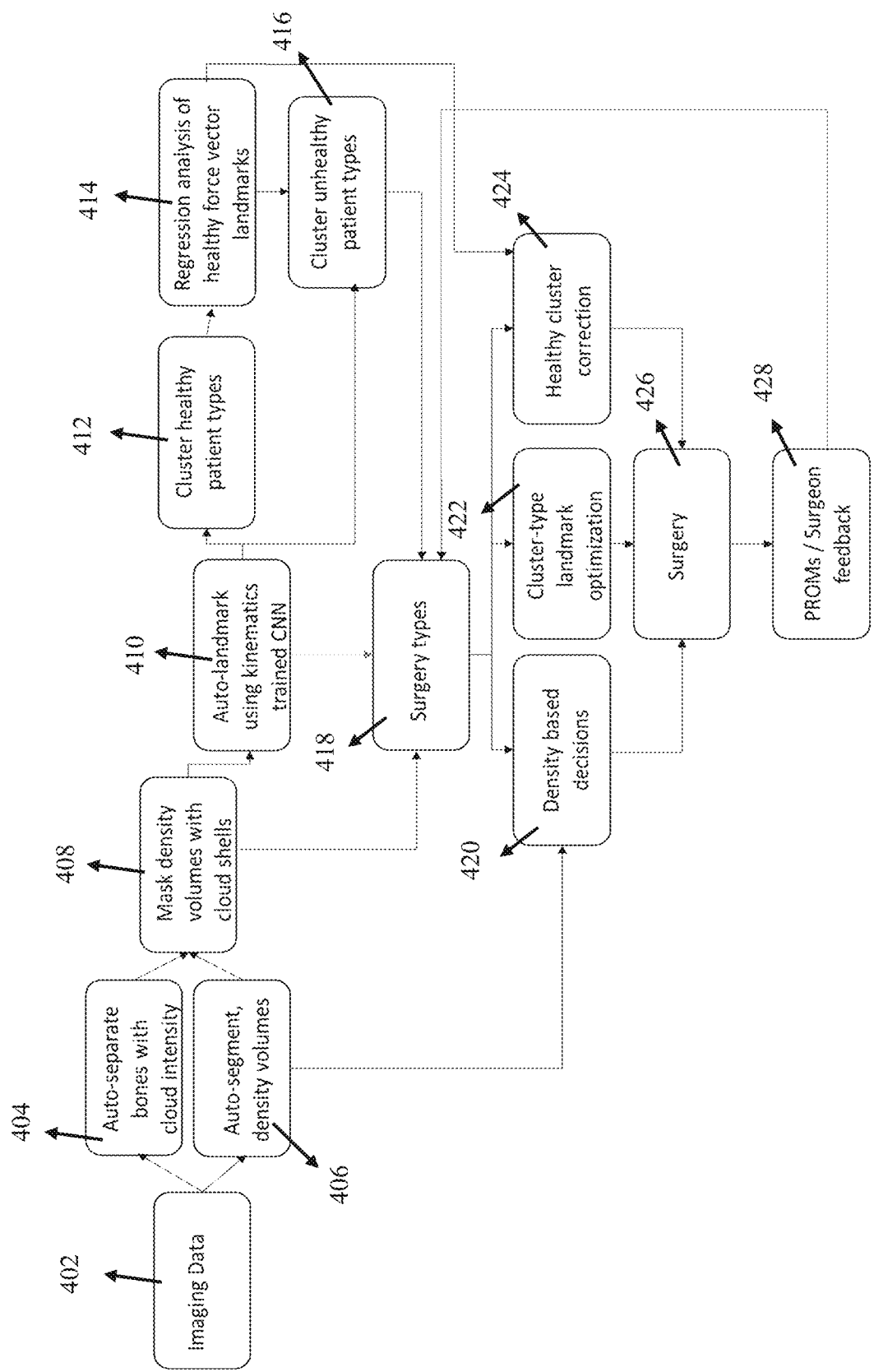
FIG. 4 illustrates a method of patient specific treatment planning, according to one or more embodiments.

FIG. 4 illustrates a method of patient specific treatment planning, according to one or more embodiments. At step 402, an image file of a region of interest of an anatomy is received. The image file comprises an image and/or a video. The image file may comprise a video file. The image and/or the video may be a medical image and/or a medical video of the region of interest. In an embodiment, the image comprises a plurality of points. In an embodiment, the plurality of points comprises one of a plurality of pixels and a plurality of voxels. The anatomy may belong to a living organism. The anatomy comprises a bodily structure of the living organism. In an embodiment, the living organism comprises an animal, a bird, a mammal, and a human being. The image file comprises one of a Digital Imaging and Communications in Medicine (DICOM) format file, a computed tomography (CT) image file and a magnetic resonance imaging (MRI) format file. The image comprises resolution of points depending on size of the plurality of points. In an embodiment, the size of the plurality of points ranges from 0.6*0.6*0.6 mm cubes to 3*3*3 mm cubes that represents one of voxels of information and pixels of information from the computed tomography (CT) image file and the magnetic resonance imaging (MRI) format file. The plurality of points comprises density information. Once the image file is received, the image file is analyzed and the density information and coordinates information of each point of the plurality of points in the image is extracted. The density information and the coordinates information are recorded in a database. Based on the density information, the coordinates information and collective information of the database, a neural network is pretrained. The database comprises pre-stored information. In an embodiment, the pre-stored information comprises at least one of a predefined virtual kinematic model, a predefined treatment location, a pre-defined treatment procedure, a predefined treatment plan, and predefined density information.

In an embodiment, point cloud information of the anatomy is created based on the density information, the coordinates information, and the pre-stored information. In another embodiment, a heat map of the anatomy is generated based on the point cloud information. The heat map indicates a segment and a foreign object (e.g., an object). The segment comprises a first segment (e.g., a dense bone), a second segment (e.g., a soft bone), etc. In an embodiment, the foreign object comprises a metal object.

Once the neural network is pretrained using the collective information available in the database, an auto separation (i.e., a virtual action) of the segment is performed, at step 404, based on the collective information in the database. In an embodiment, the auto separation is performed based on the density information (e.g., intensity). The auto separation comprises assigning a threshold value to the segment of the region of interest. The assignment of the threshold value to the region of interest comprises assigning a first threshold value to the first segment, a second threshold value to the second segment, and a third threshold value to the foreign object. In an embodiment, the first segment, the second segment and the foreign object are identified and located on the region of interest based on the density information and the coordinates information. Based on the first threshold value, the second threshold value and the third threshold value, the auto separation is performed. The auto separation comprises an edge detection. The edge detection comprises estimation of Hounsfield units in addition to the assignment of the threshold value. The estimation of Hounsfield units comprises detecting and estimating the Hounsfield units of each point of the plurality of points in the image. Based on the estimated Hounsfield units of each point of the plurality of points in the image, the segment of the region of interest is outlined automatically. In an embodiment, the first segment of the region of interest is outlined with a first color and a first identifier, the second segment of the region of interest is outlined with a second color and a second identifier. In another embodiment, the segment of the region of interest is outlined either manually, automatically, or semi-automatically.

An auto segmentation (i.e., the virtual action) is performed based on the density information at step 406. The region of interest is registered as a virtual version using an input from the neural network. The auto segmentation comprises detection of at least one of an edge and a tunnel in the region of interest. The detection of at least one of the edge and the tunnel in the region of interest comprises determining a plurality of first points of the plurality of points as at least one of the edge and the tunnel, when the plurality of first points comprises a first density value lower than a second density value of a plurality of second points. The plurality of second points is located on either side of the plurality of first points. In an embodiment, the plurality of first points comprises the first density value lower than one of 0% to 20% and 20% to 80% of the second density value of the plurality of second points.

In an embodiment, the neural network is subsequently trained using a user input from a user and the collective information available in the database. The neural network is trained to enable the server 302 to categorize and/or record the collective information under a first cluster (e.g., the healthy cluster state) comprising various sub-clusters (e.g., the physiological states) of a second cluster (e.g., the unhealthy cluster state). In another embodiment, the neural network is trained to enable the server 302 to categorize and/or record the collective information under the second cluster (e.g., the unhealthy cluster state) comprising various sub-clusters (e.g., the physiological states) of the first cluster (e.g., the healthy cluster state). In yet another embodiment, the neural network is trained to decide on the segmentation and masking of the segment of the region of interest based on the collective information available in the database without any need to execute the virtual action for the individual segment of the region of interest each time. In another embodiment, the neural network is trained to learn from the collective information available in the database and execute at least one of the virtual action, and the treatment on boundaries of the segment of the region of interest obtained using validated approaches.

At step 408, the plurality of first points (e.g., the edge, the tunnel, etc.) are masked with a processed image output of the virtual action and the plurality of first points are deleted to have only desired segments of the region of interest. The desired segments can be achieved on the region of interest by performing Boolean addition and/or Boolean subtraction.

At step 410, an auto landmarking (i.e., the virtual action) is performed to landmark the segment of the region of interest using the neural network. The landmarking comprises identifying at least one of a ligament attachment point and a tendon attachment point on the region of interest. The ligament attachment point, and the tendon attachment point may be identified to create planes and lines on the region of interest and determine couplings (e.g., mechanical axis cut versus anatomical axis cut) that are adapted to perform the treatment and recover kinematics on the region of interest. In an embodiment, the neural network is trained using predefined kinematics of the anatomy. The kinematics associated with the region of interest is analyzed and correlated with the predefined kinematics of a plurality of clusters of different physiological states in the database to identify one of the first cluster, the second cluster, etc. of the plurality of clusters of different physiological states to which the region of interest belongs. In an embodiment, the kinematics associated with the region of interest is analyzed and correlated with the predefined kinematics of the plurality of clusters of different physiological states with respect to age and an activity of daily living (ADL).

At step 412, the region of interest is categorized under the first cluster of the plurality of clusters of different physiological states upon identifying that the region of interest belongs to the first cluster. In an embodiment the first cluster comprises a healthy cluster state. At step 414, a regression analysis is performed to categorize the region of interest under the second cluster, upon identifying that the region of interest does not belong to the first cluster. In an embodiment, the regression analysis is performed to determine at least one of the parameters from the region of interest that are intended to identify a cluster from the plurality of clusters of different physiological states to which the region of interest belongs. In another embodiment, the regression analysis is further performed to determine the minimum number of parameters among total number of parameters from the region of interest that are intended to identify the cluster from the plurality of clusters of different physiological states to which the region of interest belongs.

At step 416, the region of interest is categorized under the second cluster of the plurality of clusters of different physiological states upon identifying that the region of interest belongs to the second cluster. In an embodiment the second cluster comprises an unhealthy cluster state. In another embodiment, the region of interest is categorized under a new cluster when the region of interest does not belong to one of the first cluster, the second cluster, a third cluster, etc. In yet another embodiment, the plurality of clusters of different physiological states comprises a fourth cluster based on the landmarks of the region of interest, a fifth cluster based on the tendon attachment point and a sixth cluster based on the ligament attachment point of the region of interest. In yet another embodiment, the collective information is recorded in the database with respect to a plurality of clusters of different physiological states of the living organism The auto landmarking further comprises simulating a virtual kinematic model of the region of interest and correlating the virtual kinematic model with the predefined virtual kinematic model of one of the first cluster, the second cluster, etc. to which the region of interest belongs. Once the correlation is performed, motion associated with virtual kinematic model of the region of interest is analyzed and a constraint and a constraint location for the virtual kinematic model is predicted. A first position and a first angle for at least one of the ligament attachment point and the tendon attachment point in the virtual kinematic model is determined at a first level to create/restore the kinematics in the virtual kinematic model. A second position and a second angle for at least one of the ligament attachment point and the tendon attachment point in the virtual kinematic model is then determined at a second level, when the first position and first angle fails to create/restore the kinematics in the virtual kinematic model. Based on the ligament attachment point and the tendon attachment point in the virtual kinematic model of the region of interest, the region of interest is categorized under a sub-cluster of at least one of the first cluster, the second cluster, etc. Further, based on the density information and the coordinates information the segment of the region of interest is labelled. In an embodiment, the labeling is performed to train the neural network. In an embodiment, the labeling is performed to enable the user to readily distinguish the segment of the region of interest.

At step 418, a treatment type is created based on at least one of the auto landmarking and the cluster of which the region of interest belongs. In an embodiment, the treatment type is recommended/selected based on the cluster of the plurality of clusters of different physiological states to which the region of interest belongs. The treatment type comprises a treatment procedure, a treatment location, and a treatment plan of the region of interest. In an embodiment, creating the treatment type comprises recovering the kinematics and retaining the activity of daily living (ADL) to one of the first cluster (e.g., a healthy cluster state), the second cluster (e.g., an unhealthy cluster state), the third cluster (e.g., an existing cluster state). In another embodiment, the kinematics is recovered with a compensation factor and estimating a return score to one of the healthy cluster state and the existing cluster state. In another embodiment, creating the treatment type comprises calculation of implant type used for a joint of the region of interest to prevent impingement of one of a physical device (e.g., a tool held by the user during the treatment) and a component of the physical device on a patient's body during the treatment.

Upon creating the treatment type, density-based decisions are performed at step 420 to perform a treatment on the region of interest. The density-based decisions comprise identifying a position, an angle and a cut that are to be performed on the region of interest to perform the treatment (e.g., an orthopedic implant) on the region of interest. At step 422, a landmark optimization is performed with respect to the cluster (to which the region of interest belongs) based on the treatment type created. The landmark optimization varies depending on the treatment type. At step 424, a cluster correction is performed based on the regression analysis.

Once the virtual action (i.e., the auto separation, the auto segmentation, the auto landmarking, the labeling, and creating the treatment plan) is performed, first information is recorded based on the virtual actual and the treatment performed on the region of interest. The first information comprises the treatment type (i.e., the treatment procedure, the treatment location, and the treatment plan) performed on the region of interest. In an embodiment, the first information is recorded into the database based on at least one of performing a treatment and a registration of the region of interest under a cluster of the plurality of clusters of different physiological states to which the region of interest belongs. The first information comprises remarks information of the treatment type that is performed on the region of interest. The remarks information indicates an outcome of the treatment. The outcome of the treatment comprises a first outcome (e.g., good outcome) and a second outcome (e.g., bad outcome). The remarks information further comprises a plurality of first parameters and a plurality of second parameters that contribute to the first outcome and the second outcome of the treatment, respectively. A processed image output and a processed video output, obtained as a result of the virtual action, is communicated to a user.

In an embodiment, virtual kinematic model of the region of interest and a processed image file of the region of interest is generated and simulated based on the coordinates information, the density information, and the collective information of the database. The virtual kinematic model of the region of interest comprises a three-dimensional virtual kinematic model. The three-dimensional (3D) virtual kinematic model and the processed image file of the region of interest is then communicated to a device associated with the user. The three-dimensional (3D) virtual kinematic model and the processed image file comprises the treatment procedure depicted on the region of interest. The treatment procedure comprises at least one of displaying a boundary on the region of interest, indicating a virtual cut on the region of interest, indicating a position of screws on the region of interest, etc. In an embodiment, the boundary is displayed to assist and alert the user not to perform an intervention within the boundary during the treatment.

In another embodiment, the three-dimensional (3D) virtual kinematic model and the processed image file comprises a first feature and a second feature indicated in a first color and a first indicator, and a second color and a second indicator, respectively. In yet another embodiment, the three-dimensional (3D) virtual kinematic model and the processed image file comprising the first feature and the second feature is adapted to print a three-dimensional (3D) physical incarnation of at least one of the processed image file and the three-dimensional (3D) virtual kinematic model of the region of interest. In yet another embodiment, the three-dimensional (3D) virtual kinematic model and the processed image file comprising the first feature and the second feature is adapted to track a three-dimensional (3D) physical incarnation of at least one of the processed image file and the three-dimensional (3D) virtual kinematic model of the region of interest.

In yet another embodiment, the processed image file and the three-dimensional (3D) virtual kinematic model of the region of interest is generated to provide a virtual reality version and an augmented reality version of the three-dimensional (3D) virtual kinematic model and the processed image file. In yet another embodiment, the virtual reality version, and the augmented reality version of the three-dimensional (3D) virtual kinematic model and the processed image file is adapted to enable the user to perform the treatment on the region of interest either remotely or directly. In yet another embodiment, tracking the three-dimensional (3D) physical incarnation comprises indicating the first feature with the first color, the first identifier and the second feature with the second color and the second identifier, etc. In yet another embodiment, tracking the three-dimensional (3D) physical incarnation of at least one of the processed image file and the three-dimensional (3D) virtual kinematic model of the region of interest is adapted to mimic the tool held by the user and perform the treatment remotely as directed by the user. In yet another embodiment, tracking the three-dimensional (3D) physical incarnation of at least one of the processed image file and the three-dimensional (3D) virtual kinematic model of the region of interest is adapted to track a location of the first segment (e.g., the dense bone) and depict at least one of a potential implant position, a screw position, a plate position for optimum fixation, etc. In yet another embodiment, printing the three-dimensional physical incarnation is adapted to position the three-dimensional physical incarnation and perform one of a two-dimensional (2D) spot-check and diagnosis X-rays to check orientation in surgery; and check one of a pre-op X-ray, a post-op X-ray and 2D image for extracting three-dimensional physical incarnation information.

The three-dimensional (3D) virtual kinematic model and the processed image file of the region of interest is further adapted to virtually turn-on and turn-off individual layers of the segment to identify location of various categories of body parts, make decisions and create the treatment plan. In an embodiment, the virtual kinematic model is overlaid on one of the three-dimensional (3D) physical incarnation and a physical bone of a patient. In another embodiment, the virtual kinematic model overlaid on one of the three-dimensional (3D) physical incarnation and the physical bone of the patient is seen and interacted (e.g., the treatment) with using a virtual reality environment and an augmented reality environment.

At step 426, the treatment is performed on the region of interest via the user based on at least one of the density-based decisions, the landmark optimization, and the cluster correction. In an embodiment, the user comprises at least one of a surgeon, a physician, a caretaker, a medical practitioner, and a machine. The machine comprises at least one of an automated machine and a semi-automated machine. In an embodiment, the virtual action, and the treatment on the region of interest is performed through one of the virtual reality environment and the augmented reality environment.

Once the treatment is performed, a feedback from the user (e.g., the surgeon) and a patient reported outcome measures (PROM) is received, at step 428. The feedback from the surgeon comprises confirmation from the surgeon that the region of interest belongs to the cluster (e.g., the first cluster, the second cluster, etc.) of the plurality of clusters of different physiological states, etc. The PROM is received from a patient to whom the treatment is performed. Based on the feedback from the user and the patient reported outcome measures (PROM), the second information is recorded on the database. The second information is recorded into the database, under the first cluster of the plurality of clusters of different physiological states to which the region of interest belongs, based on at least one of an outcome of the treatment and a feedback from the user. In an embodiment, the recording of the second information comprises updating the first information based on at least one of the outcome of the treatment, and the feedback from the user. Further, based on at least one of the feedback from the user and the patient reported outcome measures (PROM), the first information is updated in the database. The updating of the first information in the database comprises updating at least one of the treatment type, the plurality of first parameters, the plurality of second parameters, the plurality of third parameters, the plurality of fourth parameters, the remarks information, the plurality of clusters of different physiological states, the first physics assumptions, the second physics assumptions, etc. In an embodiment, the feedback from the user comprises at least one of confirmation and declaration from the user that the region of interest belongs to a cluster among the plurality of clusters of different physiological states.

Based on the first information updated on the database, the information is looped back to the database, and the neural network is getting trained. As the first information in the database is getting updated and updated, the neural network is capable of suggesting the treatment type suitable to the region of interest by verifying a minimum (e.g., ten parameters) number of parameters instead of looking at all the parameters (e.g., hundred parameters) that contributes to one of the first outcome and the second outcome. The collective information on the database is categorized under the plurality of clusters of different physiological states with respect to age, gender, race, geographic location, morphology, etc.

Figure 5:
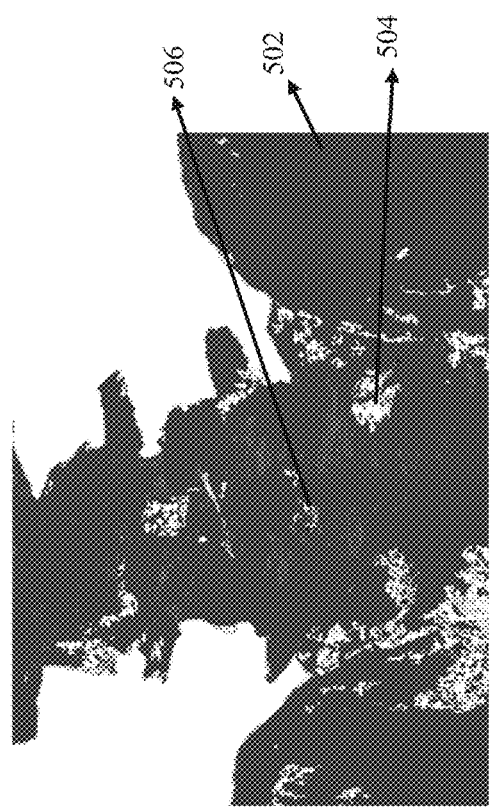
FIG. 5 illustrates a first processed image output of an auto segmentation of a segment of a region of interest, according to one or embodiments.

FIG. 5 illustrates a first processed image output of the auto segmentation of the segment of the region of interest, according to one or embodiments. The region of interest comprises the first segment 502, the second segment 504, the third segment 506, etc. The first segment 502, the second segment 504 and the third segment 506 comprise the first density value, the second density value and a third density value, respectively. The Hounsfield unit detection is performed on the region of interest to identify and locate the first segment 502, the second segment 504 and the third segment 506 (e.g., the foreign object, the tunnel, the edge, etc.). The auto segmentation, described herein, assigns the first threshold value to the first segment 502 (e.g., the dense bone), the second threshold value to the second segment 504 (e.g., the soft bone) and the third threshold value to the third segment 506 (e.g., the foreign object). In an embodiment, the first threshold value, the second threshold value and the third threshold value are assigned based on the Hounsfield unit detection on the region of interest. Since the first segment 502, the second segment 504 and the third segment 506 are assigned with the first threshold value, the second threshold value and the third threshold value, respectively, the server 302 automatically segments and displays the first segment 502, the second segment 504, the third segment 506, etc. of the region of interest. The first segment 502, the second segment 504, the third segment 506, etc. is outlined and indicated with different colors and different identifiers to enable the user to readily distinguish and identify the first segment 502, the second segment 504, the third segment 506, etc.

The Hounsfield unit detection is further performed to determine at least one of the edge and the tunnel on the region of interest. The density value of the plurality of points on the image file of the region of interest is determined. The plurality of first points of the plurality of points is determined as at least one of the edge and the tunnel on the region of interest when the plurality of first points comprising the first density value is lower than the second density value of the plurality of second points. The plurality of second points is located on either side of the plurality of first points. In an embodiment, the plurality of first points comprises the first density value lower than one of 0% to 20% and 20% to 80% of the second density value of the plurality of second points.

Figure 6:
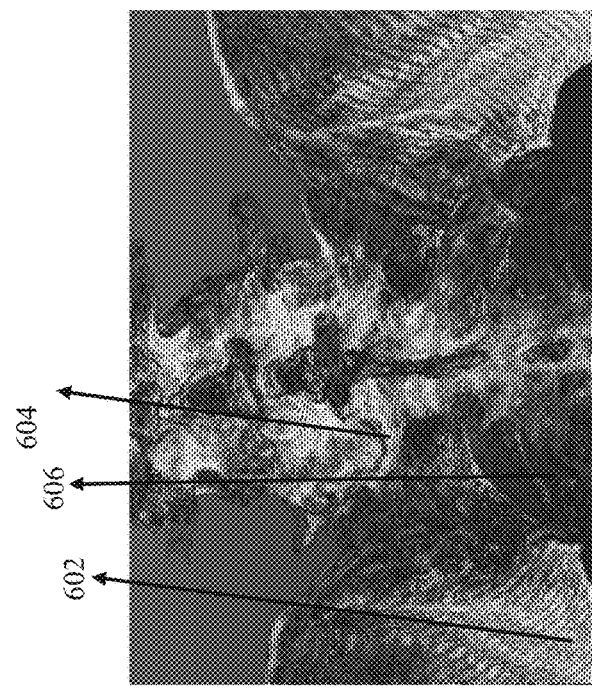
FIG. 6 illustrates a second processed image output of point cloud information of a region of interest, according to one or more embodiments.

FIG. 6 illustrates a second processed image output of the point cloud information of the region of interest, according to one or more embodiments. The image file of the region of interest is received by the server 302. The image file comprises the image. The density information and the coordinates information of the plurality of points of the image is extracted. The density information and the coordinates information are used to create the point cloud information of the region of interest. The point cloud information comprises the bunch of points. The point cloud information is not a solid surface object. The point cloud information further does not comprise connections between the bunch of points. The point cloud information allows the user to mask the plurality of second points around the plurality of first points in the point cloud and delete the plurality of second points. In an embodiment, the plurality of second points is deleted automatically. In another embodiment, the plurality of second points is deleted semi-automatically. In yet another embodiment, the plurality of second points is deleted manually. In yet another embodiment, the edge and/or the tunnel 606 is identified among the bunch of points of the point cloud information between the first segment 602 (e.g., the first bone), the second segment 604 (e.g., the second bone), etc. of the region of interest. The first segment 602, the second segment 604, the edge and/or the tunnel 606 is indicated with different colors and different identifiers to enable the user to readily identify and distinguish the first bone, the second bone and the edge. A heat map of the anatomy is generated based on the point cloud information. The heat map may indicate a location of a first bone, a second bone, a first object, a second object, soft tissues, hemorrhage, blockage, cancerous cells, and a foreign object within the region of interest.

The user is then allowed, by the server 302, to mask the plurality of second points of the first bone and the second bone and delete the plurality of first points of the edge and/or the tunnel. Once the edge and/or the tunnel 606 is deleted from the region of interest, the first segment 602 (e.g., the first bone) and the second segment 604 (e.g., the second bone) on the region of interest is left on the point cloud information. In an embodiment, the region of interest is labelled by at least one of automatically, semi-automatically and manually. In another embodiment, the region of interest is labelled from one of top to bottom, bottom to top, left to right and right to left. For a first instance, in case of labelling the region of interest from the top to bottom, then a skull is a labelled as Z and a foot is labelled as –Z. For a second instance, in case of labelling a left knee and right knee, the left knee is labelled as +X and right knee is labelled as –X. For a third instance, when the treatment plan for the left knee is created automatically, the treatment plan (e.g., angled cut, etc.) for the right knee is mirrored and created automatically. Similarly, when the treatment plan is created for a left hand, the treatment plan for a right hand is mirrored and created automatically.

Figure 7:
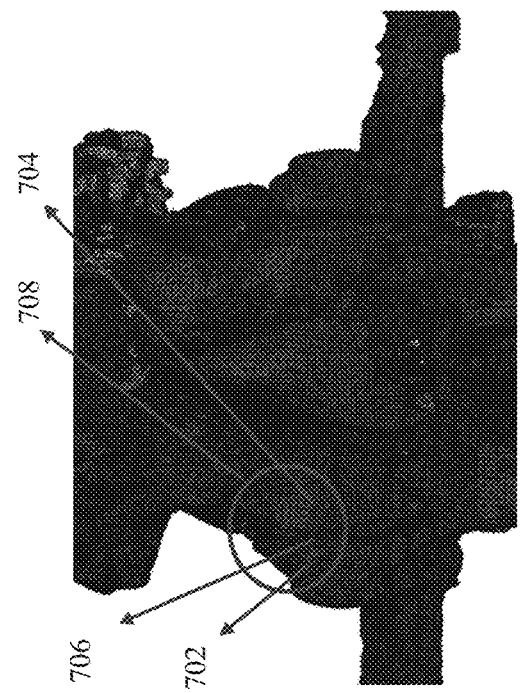
FIG. 7 illustrates a third processed image output of a virtual action, according to one or more embodiments.

FIG. 7 illustrates a third processed image output of the virtual action, according to one or more embodiments. The point cloud information is generated from the image file received. The point cloud information comprises the bunch of points that are not connected with each other. The point cloud information comprises shells and encapsulates the first segment, the second segment, the third segment, etc. Masks (i.e., the shells) on the point cloud information are taken and enforced on top of the first processed image output of the auto segmentation (e.g., FIG. 5) to get the third processed image. The third processed image output depicts the first segment with the first color and the first identifier (e.g., a first label), the second segment with the second color and the second identifier (e.g., a second label), and the third segment with the third color and the third identifier (e.g., a third label). The first segment, the second segment and the third segment comprising the first density value, the second density value and the third density value respectively is readily identified based on the first color and the first identifier (e.g., a first label), the second segment with the second color and the second identifier (e.g., a second label), and the third segment with the third color and the third identifier (e.g., a third label) respectively. At 708, the third processed image output clearly depicts the edge/the tunnel 706 between the first segment 702 and the second segment 704 of the region of interest.

For a first instance, in an orthopedic implantation, based on the location of the first segment (e.g., the dense bone), the user is allowed to figure out where to place trajectories and find entry points of screws. In an embodiment, based on the location of the first segment (e.g., the dense bone), the user is allowed to place the screw and create a sphere around a sphere of influence (e.g., four or five millimeters). The plurality of points that touch the sphere are determined as entry points and the trajectories are created and from the plurality of points, the neural network determines whether the landmarks are on the region of interest. In an embodiment, once the first cluster (e.g., the dense bone) relevant to the region of interest is identified, the trajectories for the entry points and exit points of the screw are generated and a factorial of all combinations of the entry points and the exit points is generated. In an embodiment, the trajectories, and the factorial of all combinations of the entry points and the exit points are filtered based on at least one predefined rule. The predefined rule is set with respect to at least one of a thread engagement to the first segment (e.g., the dense bone), diameter of the screw contacting the first segment (e.g., the dense bone), length of the screw engaging a volume of the dense bone, etc. In an embodiment, the trajectories, and the factorial of all combinations of the entry points and the exit points are filtered and reduced to a smaller subset based on neural network driven solutions to recommend/provide the treatment plan to the user. A plurality of lines of the dense bone along its path are determined based on parameters of at least one of a pitch of the screw, a diameter of the screw and the length of the screw. Based on the parameters, the user is able to recognize and identify a type of screw to use, a thread of the screw and the trajectory for optimum fixation.

For a second instance, in an unicondylar knee arthroplasty, the exact location of the dense bone in the third processed image output enables the user to identify the dense bone among the region of interest and to make a predefined cut (e.g., a halfmoon shape cut) on exactly the dense bone (e.g., tibia), instead of inadvertently making the predefined cut on the soft bone. Inadvertently creating the predefined cut on the soft bone impacts a micro motion or a larger motion on the region of interest.

For a third instance, the third processed image output enables the user to identify readily a primary implant (e.g., the foreign object) from the region of interest. The third processed image output further enables the user to discover readily the first segment (e.g., the dense bone) in which the primary implant is fixed earlier, and screw type attachments for revision surgery once the primary implant is removed. In an embodiment, removing the primary implant from the region of interest may comprise removing stock of the dense bone from the region of interest as the primary implant has fixed to the first segment (e.g., the dense bone) and the first segment remaining on the region of interest is difficult to determine with imaging techniques. The third processed image output depicts the first segment remaining on the region of interest even after removing the primary implant and the stock of the dense bone and enables to register and perform the revision surgery.

Figure 8:
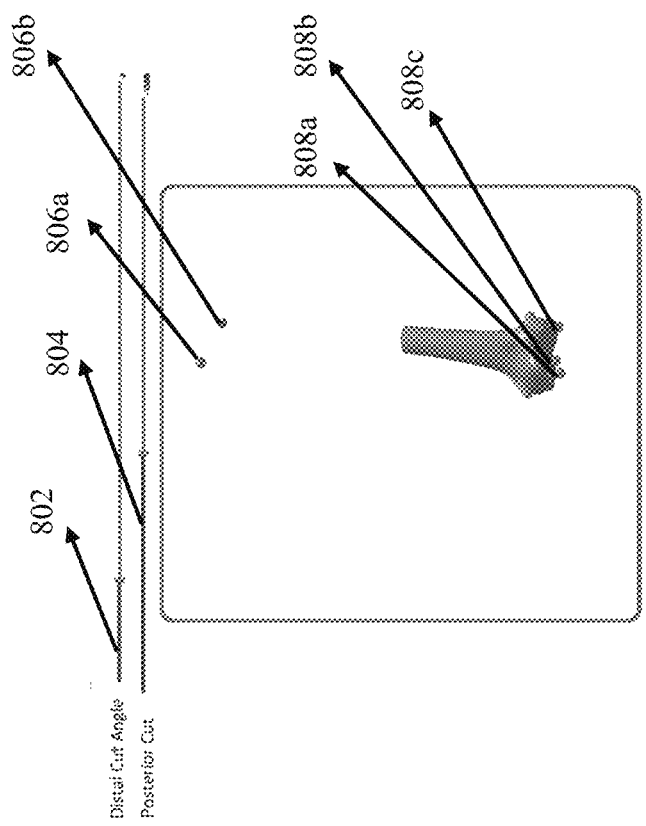
FIG. 8 illustrates an interface view during an auto landmarking, according to one or more embodiments.

FIG. 8 illustrates an interface view during the auto landmarking, according to one or more embodiments. The interface view (shown in FIG. 8) depicts one or more sliders 802, 804 of one or more parameters that are intended to adjust the kinematics on the region of interest. The one or more sliders 802, 804 allow the user to adjust the one or more parameters during the treatment (e.g., surgery). The parameters comprise at least one of but not limited to a depth of cut, a cut angle, the treatment location etc. The interface view further depicts the plurality of first points 806a, 806b of the first segment (e.g., hip) and the plurality of second points 808a, 808b, 808c of the second segment (e.g., knee). 806a is a hip center and 806b is a lesser trochanter location. The lesser trochanter defines a posterior plane. The lesser trochanter is where muscles attach to flex and extend. The user is enabled to adjust the kinematics associated with the plurality of first points 806a, 806b and the plurality of second points 808a, 808b, 808c by adjusting the one or more sliders 802, 804 on the interface view on the fly (i.e., during the treatment). In an embodiment, the system automatically adjusts the kinematics by automatically analyzing the region of interest and adjusting the one or more sliders based on the analysis for an optimum treatment. In another embodiment, the user is enabled to adjust the kinematics on the fly (i.e., during the treatment) that are automatically set by the system.

Figure 9:
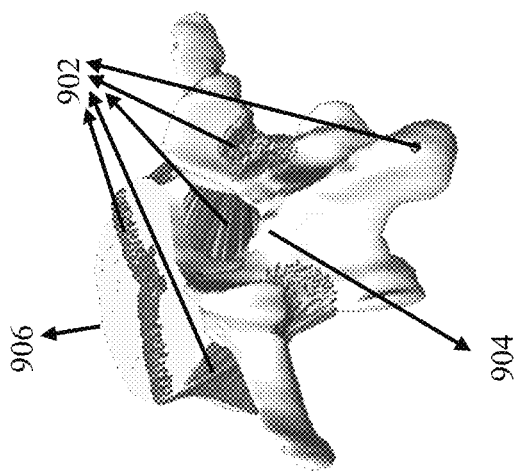
FIG. 9 illustrates a fourth processed image output of a virtual action depicting a treatment procedure on a region of interest, according to one or more embodiments.

FIG. 9 illustrates a fourth processed image output of the virtual action depicting the treatment procedure on the region of interest, according to one or more embodiments. The fourth processed image output shows a potential location 902 for the screw. The fourth processed image output may depict the trajectories for path of the screw. The fourth processed image output further shows the entry points of the screw and exit points of the screw. With respect to FIG. 9, the entry points are towards front side 904 of the region of interest (e.g., the hip) and the exit points are away from the front side (i.e., back side 906) of the region of interest (e.g., the hip). In an embodiment, the fourth processed image output shows the potential location of the screw. In an embodiment, the potential location of the screw is determined and indicated based on the density value associated with the region of interest (e.g., the hip), the length of the screw, the diameter of the screw and the pitch of the screw. The fourth processed image output further indicates number of threads in the screw that are to be fixed in the region of interest.

For an instance, when the screw is of one millimeter, the fourth processed image output comprises a first number of the potential locations. When the screw is of eight millimeter, the fourth processed image output comprises a second number of the potential locations. The first number of the potential locations is higher than the second number of the potential locations, as the screw of one millimeter can fit most of the region of interest when compared to the screw of eight millimeter.

Figure 10A:
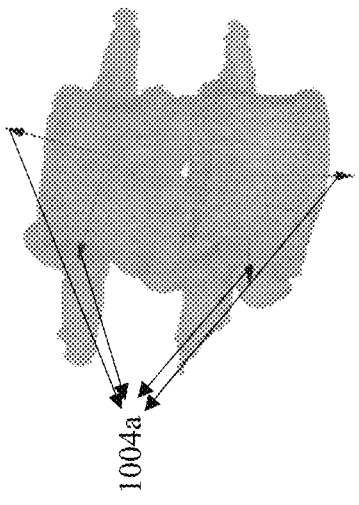
FIGS. 10a and 10b shows a region of interest in an unhealthy cluster state and a healthy cluster state respectively, according to one or more embodiments.
Figure 10B:
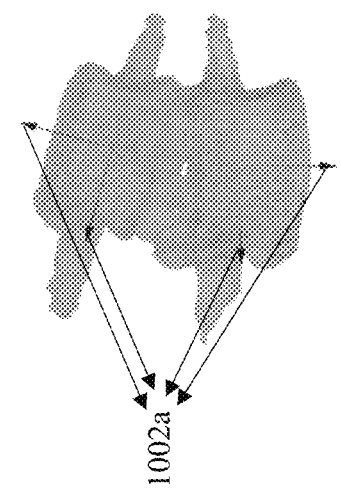

FIGS. 10a and 10b shows the region of interest in the unhealthy cluster state and the healthy cluster state respectively, according to one or more embodiments. The region of interest shown in FIGS. 10a and 10b is a first spinal bone in the unhealthy cluster state (e.g., a scoliosis state) and the healthy state, respectively. The first spinal bone is restored to the healthy cluster state from the scoliosis state based on the predefined virtual kinematic model associated with the healthy cluster state. FIGS. 10a and 10b dictates ligament and muscle lines acting on the first spinal bone to realign the unhealthy cluster state to the healthy cluster state. The ligament and muscle lines (e.g., tension) acting on the first spinal bone of the healthy cluster state is used to calculate and create the treatment plan (e.g., tension, muscle contraction, etc.) for the region of interest (i.e., the first spinal bone). The ligament and muscle lines acting on the first spinal bone of the healthy cluster state is used to track the trajectories for the screw. Further arrows 1002a, 1004a shown in FIG. 10a and 10b depicts original coordinates of the first spinal bone prior to realigning the first spinal bone with a coordinate determination engine.

The coordinates determination engine comprises a physics engine that calculates an intervention location in polar coordinates rather than the original coordinates in order to perform the intervention and restore the first spinal bone to the healthy cluster state based on the predefined virtual kinematic model associated with the healthy cluster state. In the predefined virtual kinematic model, ligament and spinal spacing comprise optimization in six degrees of freedom. The ligament and muscle lines acting on the first spinal bone and the arrows 1004a as indicated in FIG. 10b shows an optimum line length of the ligament and muscle lines, the polar coordinates and elasticity that is to be achieved so as to restore the first spinal bone from the scoliosis state to the healthy cluster state.

Figure 11:
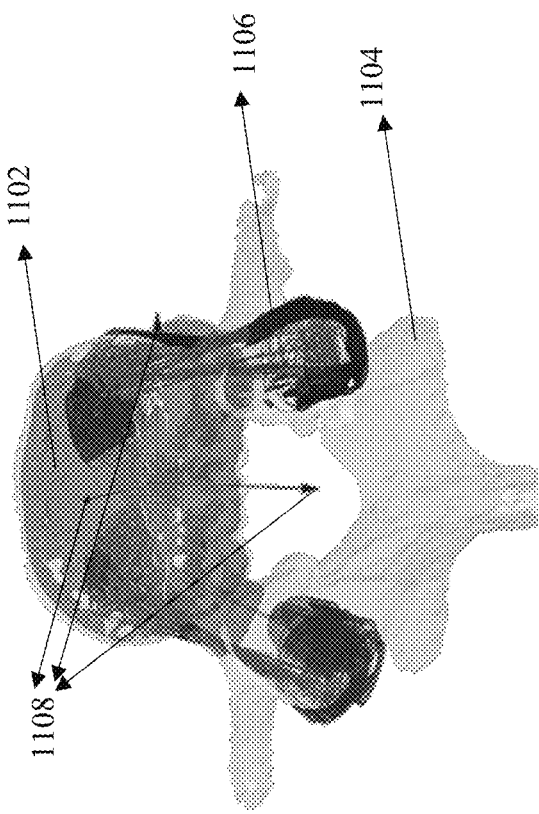
FIG. 11 illustrates an interface view of tracking a three-dimensional virtual kinematic model of a region of interest and depicting a treatment plan on the region of interest, according to one or more embodiments.

FIG. 11 illustrates an interface view of tracking the three-dimensional virtual kinematic model of the region of interest and depicting the treatment plan on the region of interest, according to one or more embodiments. The three-dimensional virtual kinematic model of the region of interest is generated and simulated based on the coordinates information and the density information extracted from the image file. The three-dimensional virtual kinematic model comprises the first segment 1102 (e.g., the first bone), the second segment 1104 (e.g., the second bone), and the third segment 1106 (e.g., the foreign object). The first segment 1102, the second segment 1104, and the third segment 1106 are indicated using the first color and the first identifier, the second color and the second identifier and the third color and the third identifier, respectively. The first segment 1102, the second segment 1104, and the third segment 1106 are readily distinguished to the user. The interface view depicts the ligament and muscle lines and arrows 1108 indicating the polar coordinates on the region of interest. The interface view further depicts at least one of a grouping of potential implant, the screw and plate position etc. on the region of interest. In an embodiment, the grouping implant, the screw, and the plate position are indicated with a fourth color, a fifth color, and a sixth color, respectively to readily identify and distinguish between the grouping implant, the screw, and the plate position.

Figure 12A:
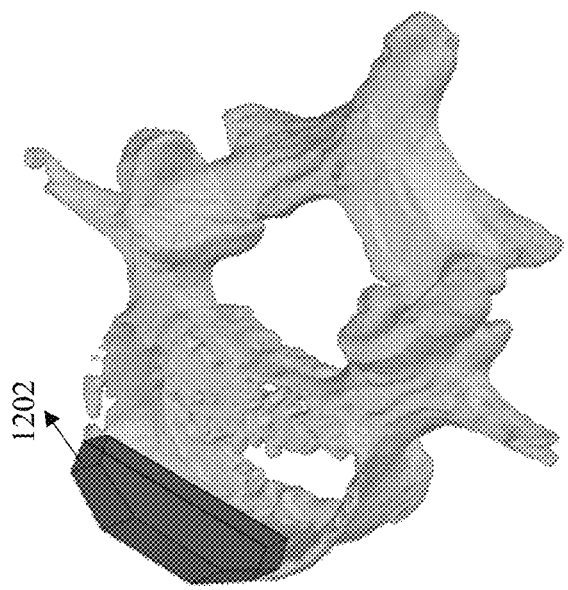
FIGS. 12a and 12b illustrates an interface view to a user that depicts an implant placement and adjusting/orienting the implant placement to an optimal location on a region of interest, according to one or more embodiments.
Figure 12B:
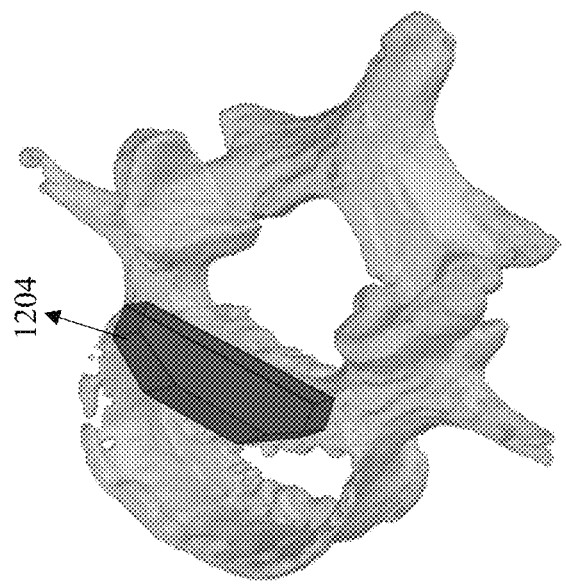

FIGS. 12a and 12b illustrates an interface view to the user that depicts an implant placement and adjusting/orienting the implant placement to an optimal location on the region of interest, according to one or more embodiments. The region of interest shown in FIGS. 12a and 12b is a second spinal bone. In an embodiment, the region of interest may be any part and/or any portion (e.g., the shoulder, the knee, the spine, etc.) of the living organism. The information extracting unit 310 of the server 302 extracts the coordinates information and the density information associated with the region of interest once the image file of the region of interest is received. The server 302 through the communication unit 330 communicates the processed image output to the device associated with the user.

The processed image output depicts the first segment (e.g., the dense bone), the second segment (e.g., the soft bone), the third segment (e.g., the foreign object), etc. based on the density information, the kinematics, the coordinates information, and the point cloud information of the region of interest. The processed image output also depicts a first location, a second location, a third location, etc. on which the first segment, the second segment, the third segment are located and/or positioned, respectively. FIG. 12a depicts the implant placement at the first location 1202. The first location may be a random location selected/guessed by the user assuming that the first location is the location of the dense bone. The virtual kinematic model generation unit generates the virtual kinematic model of the region of interest (e.g., the second spinal bone) having the implant placement at the first location and simulates/runs the virtual kinematic model of the region of interest to determine whether the first location is the optimal location.

In an embodiment, the region of interest comprises a plurality of dense bones (e.g., a first dense bone, a second dense bone, a third dense bone, etc.). In another embodiment, the first segment (e.g., the dense bone) comprises the first dense bone, the second dense bone, the third dense bone, etc. The processed image output also depicts a fourth location, a fifth location, a sixth location, etc. on which the first dense bone, the second dense bone, the third dense bone are located, respectively. The optimal location for the implant placement on the region of interest may vary from the first location, when the region of interest comprises the plurality of dense bones with different density values (i.e., when the region of interest comprises the first dense bone, the second dense bone, the third dense bone, etc.).

FIG. 12b depicts the implant placement adjusted/oriented to the optimal location 1204 based on at least one of the kinematics, the point cloud information, the density information, and the coordinates information. The optimal location may comprise one of the fourth location, the fifth location, the sixth location, etc. The optimal location may comprise optimum attachment points. In an embodiment, the optimal location of the implant placement provides movement of six degrees of freedom. The optimal location is determined and identified using a simulation. In an embodiment, the simulation comprises a Monte Carlo Simulation. In another embodiment, the optimal location is determined and identified by the server 302, considering the implant having maximum contact with the dense bone of the region of interest. The implant having the maximum contact with the dense bone of the region of interest provides optimum support and fixation. The optimal location comprises a location of densest bone possible among the region of interest.

In an embodiment, the interface view allows the user to select the optimal location (e.g., the fourth location, the fifth location, the sixth location, etc.) from the region of interest for the implant placement. In another embodiment, the interface view allows the user to select at least one of the first dense bone, the second dense bone, the third dense bone, etc. for the implant placement (i.e., the interface view allows the user to select the optimal location for the implant placement based on the density values). In yet another embodiment, the interface view allows the user to move the implant virtually in XYZ plane and rotate/orient the implant about its axis to have the maximum contact with the dense bone of the region of interest and the optimum support. In yet another embodiment, the interface view allows the user to change a size of the implant to fit to the region of interest. In yet another embodiment, the interface view allows the user to change the size of the implant with respect to the size of the dense bone on the region of interest. In yet another embodiment, the interface view allows the user to change the size of the implant with respect to the size available from a manufacturer of the implant.

In yet another embodiment, the interface view allows the user to change the size of the implant with respect to population (e.g., United States Population, Asian population, etc.) to which the region of interest belongs and with respect to aspect ratio. In yet another embodiment, the interface view allows the user to orient the implant on the region of interest to a first angle and determine whether the implant overhangs and/or under hangs on the region of interest and prevent the implant from protruding/hitting at least one of veins, arteries, bones, etc. on the region of interest. The interface view also depicts at least one treatment procedure indicating at least one of the size of the implant, the orientation, the optimal location etc. The interface view further enables the user to select the at least one treatment procedure that provides the implant placement with the optimum fixation at the region of interest. The optimal location may comprise a first optimal location, a second optimal location etc. The interface view allows the user to perform the implant placement subsequently at the second optimal location, when the implant placement performed at the first optimal location fails to restore the kinematics in the region of interest. The optimal location for the optimum fixation on the region of interest is updated back on the database by the information recording unit. In yet another embodiment, the interface view allows the user to place an Anterior cruciate ligament (ACL), a medial collateral ligament (MCL) etc. at appropriate location in case of ACL, MCL tear etc. and the information recording unit updates/loops back the collective information on the database.

Figure 13:
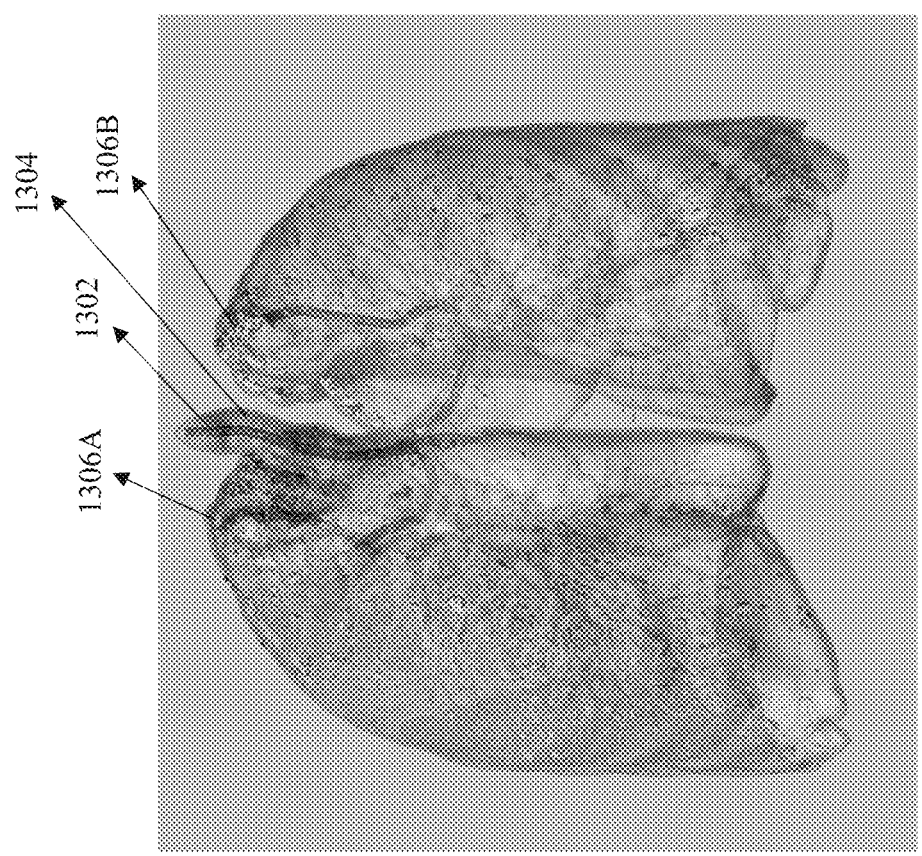
FIG. 13 illustrates an automatic generation of path to a region of interest, according to one or more embodiments.

FIG. 13 illustrates an automatic generation of path to a region of interest, according to one or more embodiments. The system upon receiving an image file of the region of interest registers the region of interest as a virtual version. The virtual version is replication of a physical version of the region of interest as a digital version. The virtual version may be in a two-dimensional format or a three-dimensional format. The virtual version is utilized, by the system, to navigate and analyze the region of interest in any direction. In an embodiment, the virtual version is utilized, by the system, to analyze the region of interest in six degrees of freedom. In another embodiment, the virtual version of the region of interest enables the user to select the region of interest for which the path is to be created.

The system comprises a virtual measurement tool. The virtual measurement tool analyses the virtual version of the region of interest in six degrees of freedom and determines virtual measurements of the region of interest. The virtual measurements comprise inner diameter, length, width, breadth, height, and in-depth measurements of the region of interest. The system analyses the virtual measurements and creates a path to an area of interest or an object within the region of interest. The system depicts the path with appropriate depths and measurements. The path created may be used, by the user, to execute the treatment without any error. In an embodiment, the system creates multiple paths to the area of interest or the object within the region of interest. The multiple paths are shown in distinct colors in order to be readily identified by a user.

The system may also analyze the multiple paths and estimate the virtual measurements associated with the multiple paths. The system suggests and recommends the path among the multiple paths based on analyzing the virtual measurements associated with the multiple paths. In an embodiment, the system recommends the path based on the virtual action or treatment to be performed on the region of interest. For example, as shown in FIG. 13, consider the user is planning to perform a treatment or surgery on lungs. The system as soon as receives the image file of the lungs of a patient, creates the virtual version in at least one of a two-dimensional format and a three-dimensional format. The system then determines the virtual measurements of the lungs. The system also detects for anomalies or defects (e.g., cancer, tumor, blood clot, hemorrhage, etc.). The system then detects an exact location, exact position, exact angle, and exact orientation of at least one of the anomaly, the defect, an object, an area of interest, and a segment within the region of interest.

The system then creates the path to approach or reach at least one of the anomaly, the defect, the object, the area of interest, and the segment detected within the region of interest. The area of interest may be the area having low density value or the area having high density value (e.g., the region having cancerous cells, tumor, etc.) within the region of interest. The system depicts the path to the user with the virtual measurements that are necessary for executing the treatment. The virtual measurements may comprise diameter of the path, depth of the path, length, etc. In an embodiment, the system creates or recommends the path based on the treatment (e.g., surgery) to be done on the region of interest. In another embodiment, the system creates or recommends the path based on an instrument (e.g., a flexible robot, a rigid robot, a cutting tool, etc.) to be utilized in the treatment.

The system may analyze the defect or anomaly in the region of interest. The database may store information regarding defects that may occur in the region of interest. The database may further store the corresponding list of treatments and instruments utilized for curing the defect in the region of interest. The system accesses the database and determines the treatment and the instrument utilized in curing the defect. The system then creates or recommends the path considering the treatment and the instrument.

The system may also record the virtual measurements within the virtual surgery generated alignment guide. In an embodiment, the system records the virtual measurements within a tracking feature (e.g., quick response (QR) code, a tracking code, radio wave frequencies, etc.) of the virtual surgery generated alignment guide. The tracking feature renders the information of at least one of the virtual measurements, surgery information, and updated surgery information to the user as treatment notes (e.g., surgical notes) when the user scans the tracking feature. In an embodiment, the user can scan the tracking feature using a camera or a scanning device.

The system may also create the paths considering protrusion length. In another embodiment, the system creates the paths to the region of interest, using computer aided design (CAD), considering prevention of artery damage or soft-tissue damage.

FIG. 13 shows a path 1302 created for the right and left lungs through a bronchi 1304. The path 1302 is created herein to target areas 1306A and 1306B. The target areas 1306A and 1306B herein may be determined from the density maps and point cloud information generated by the system. The target areas 1306A and 1306B may be high density areas or low density areas. The system creates the path 1302 with suitable measurements in such a way to support the surgeon during the surgery. In an embodiment, the system creates the path through various invasive or less invasive routes. The path 1302 may be direct paths or orifice openings which can be used in navigation or robotic surgery applications, as well as manual surgery approaches. The path 1302 can further support the surgeon's understanding of the unseen paths. The path 1302 are adapted to generate reliable repeat surgeries based on surgeon and engineering agreed safety rules. The database may also comprise surgeon and engineering agreed safety rules. The path 1302 generated by the system can be utilized for educational, practice, or in surgery applications.

Figure 14A:
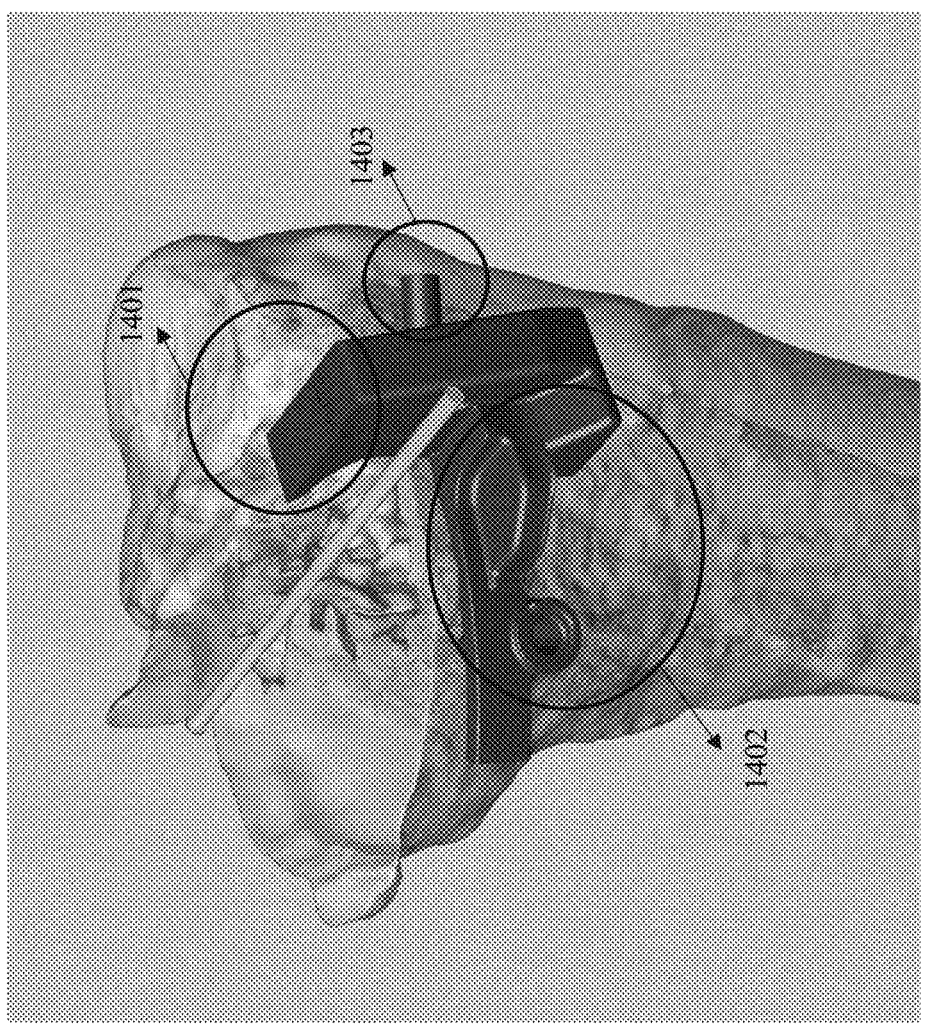
FIGS. 14a and 14b illustrate a virtual surgery generated alignment guide attached to a region of interest, according to one or more embodiments.
Figure 14B:
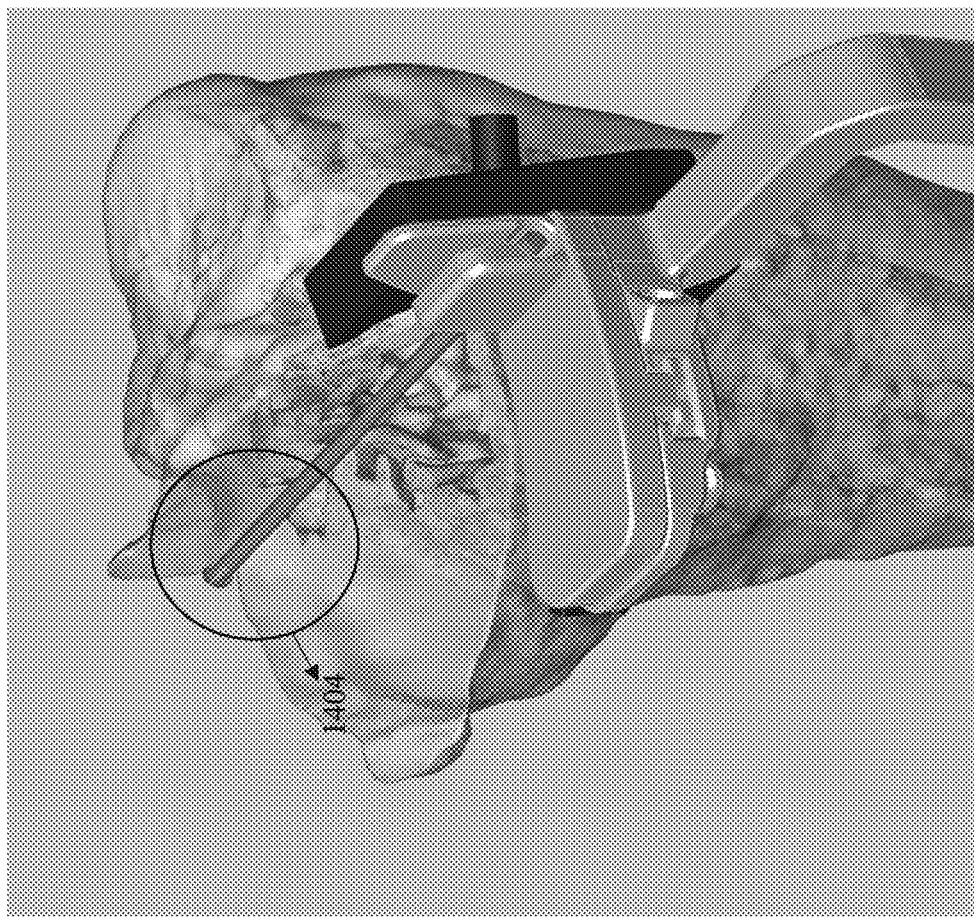

FIGS. 14a and 14b illustrate a virtual surgery generated alignment guide attached to a region of interest, according to one or more embodiments. The virtual surgery generated alignment guide is generated as a virtual version as well as a physical version. The virtual surgery generated alignment guide is designed and generated to fit the geometry reproducibly. The virtual version is nothing but a digital version of the virtual surgery generated alignment guide in at least one of a two-dimensional format, and a three-dimensional format. The physical version is nothing but a physical incarnation of the virtual surgery generated alignment guide. The virtual version of the virtual surgery generated alignment guide is adapted to check and confirm matching of the virtual surgery generated alignment guide with the region of interest. The matching performed effectively and instantly registers the location and orientation of the region of interest or other anatomy to the virtual version. The registration of the surface of the region of interest and the exact matching eliminates a need for registration of physical landmarks in surgery. The registration further eliminates the need for the option to check an important landmark compared to the virtual surgery generated alignment guide for in-surgery check. The registration is further utilized to reduce time spent preparing navigation or robotic tools in aid of surgery.

The virtual surgery generated alignment guide is attached to a physiological feature based on DICOM image Boolean subtraction. The virtual surgery generated alignment guide is attached to the physiological feature of the region of interest to get a reproducible fit. The virtual surgery generated alignment guide is attached at a location where surgical incision has created enough opening to expose the medical image predicted surface. In an embodiment, the virtual surgery generated alignment guide is attached to an anteromedial proximal tibia surface distal to a cartilage region. In another embodiment, the virtual surgery generated alignment guide is attached to an anteromedial distal femur surface outside a cartilage area to reproducibly fit the surface of the region of interest. Once the virtual surgery generated alignment guide is attached, the anatomy location is known to the manual or navigation tracking device. The manual or navigation tracking device may be affixed through the tools in the virtual surgery alignment guide. As soon as the anatomy location is known, a reproducible cut which was preplanned in the virtual environment can be executed.

The virtual surgery generated alignment guide placed on the patient can be a mirror image of a remote anatomy representation. The mirror image of the remote anatomy representation is used to operate or cut the anatomy in at least one of a virtual reality representative model, an augmented reality representative model, and a physical representative model. The treatment (e.g., cut, burr, operation, surgery, etc.) made on the anatomy can be used to show the remote OR robot. In an embodiment, the treatment (e.g., cut, burr, operation, surgery, etc.) made on the anatomy can be used to teach or train the remote OR robot on the approach and features to cut. The remote OR robot may comprise a system mimicking what the surgeon is doing remotely using the virtual surgery generated alignment guide on the patient. The anatomical cut or operation performed on the virtual reality representative model is performed using haptic solutions. In an embodiment, the anatomical cut or operation performed on the physical representative model is intuitive.

Figure 15A:
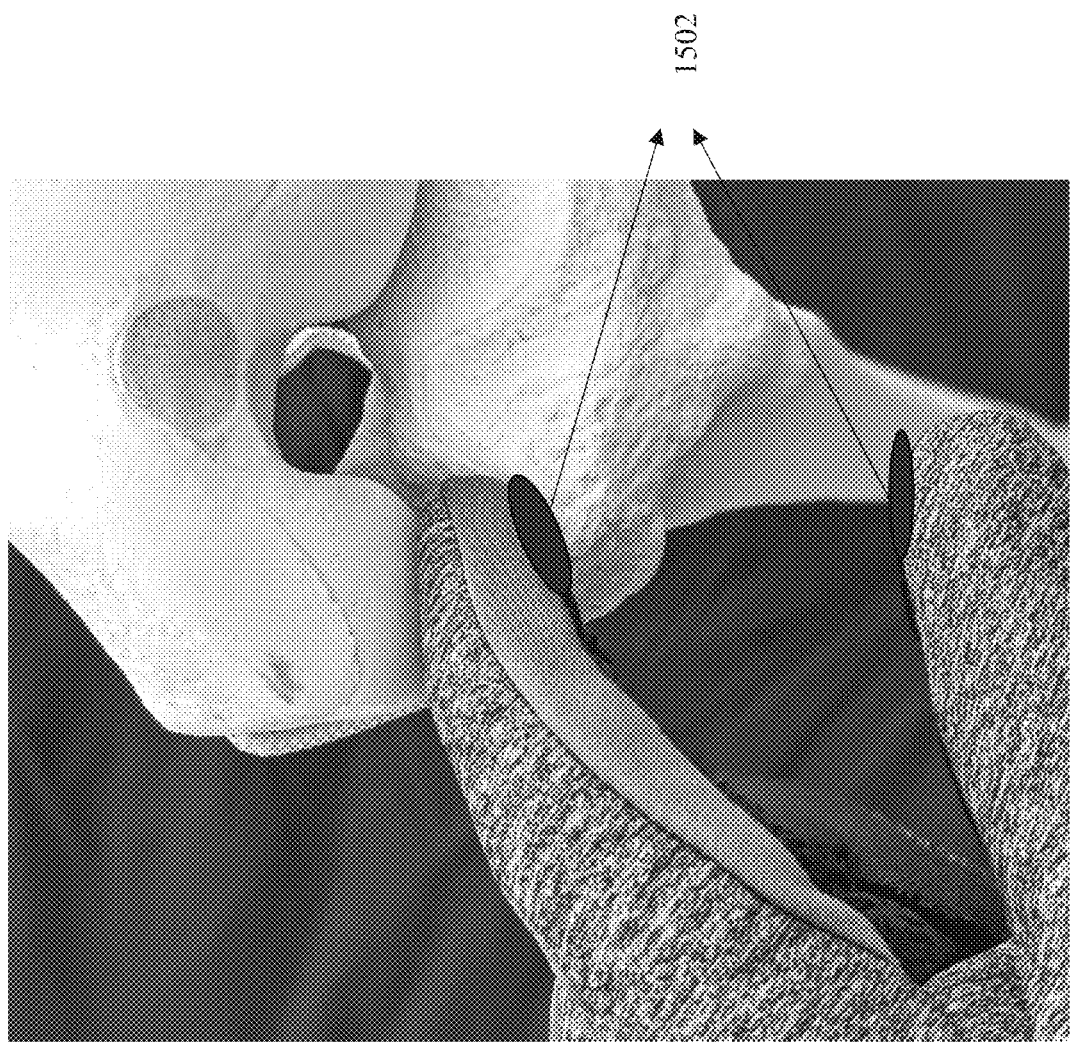
FIGS. 15a and 15b illustrates a surface compliance device, according to one or more embodiments.
Figure 15B:
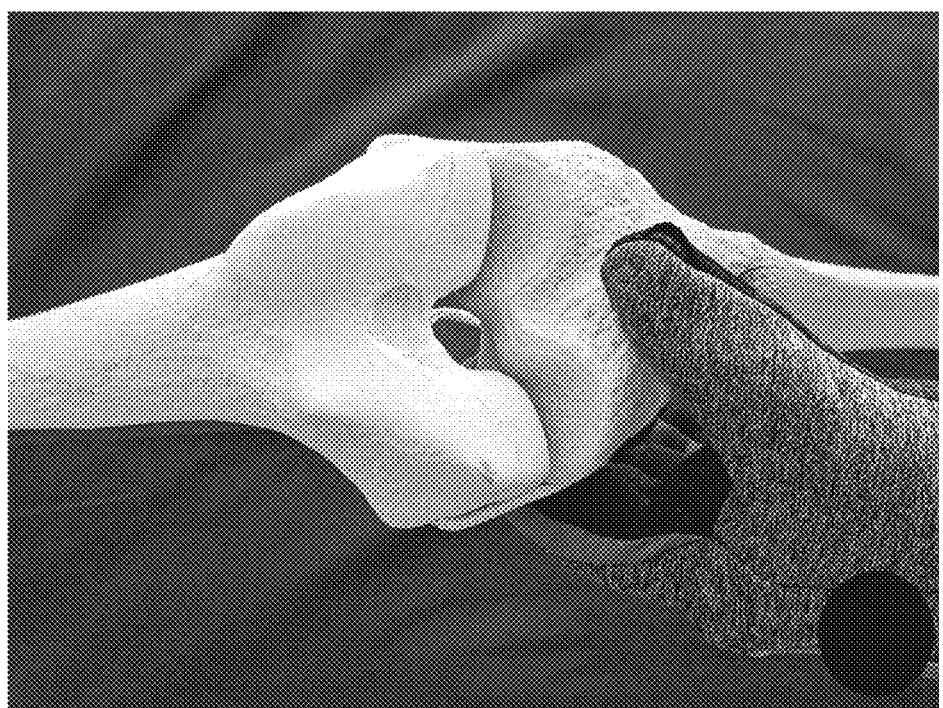

The virtual surgery generated alignment guide shown in FIGS. 15a and 15b comprises a first portion and a second portion. The first portion is adapted to attach the virtual surgery generated alignment guide exactly to an optimum region on the region of interest. In an embodiment, the first portion is adapted to fix the virtual surgery alignment guide to fit the anatomy in only one way. The second portion comprises attachment means (as shown in FIG. 14a). The attachment means comprises a first tool 1401, a second tool 1402, and a third tool 1403 as shown in FIG. 14a. The first tool 1401 is adapted to match the region of interest in relation to the anatomy. The first tool 1401 may also be adapted to recognize and identify the region of interest. The first tool 1401 may comprise unique identifiers (e.g., unique ID numbers) to recognize and match the region of interest in relation to the anatomy.

The second tool 1402 is adapted to hold and fasten an external instrument. The external instrument comprises at least one of a cutting guide, an alignment guide, a cutting tool, a semi-automated instrument, an automated instrument, and a manual instrument. The external instrument may further comprise one of a camera, and a sensor. The sensor may be utilized in treatment of the region of interest. The second tool 1402 may also be adapted to match a cutting guide. The cutting guide may be an automated cutting guide, or a manual cutting guide. The third tool 1403 comprises an attachment location for holding navigation instruments or robotic instruments such as a reflective ball tracked by an infra-red (IR) camera. The navigation instruments are adapted to show the surgical navigation or robotic system the location and orientation of the virtual surgery generated alignment guide.

In an embodiment, the virtual surgery generated alignment guide comprises a tracking feature. The tracking feature may be a printed tracking feature. The printed tracking feature may be a colored quick response (QR) code. The colored QR code comprises at least one of surgery information, updated surgery information, and surgery notes. The surgery information comprises information regarding any surgery done previously on the region of interest. The surgery information may comprise patient specific information. The updated surgery information comprises strategy, modifications, and updates performed by the surgeon while treating the region of interest. The surgery notes comprise reminders, or any activities to be followed by the surgeon while providing treatment (e.g., operating) on the region of interest.

The tracking feature may be scanned by a user using a camera or a scanning device. The tracking feature, when scanned, virtually displays information such as cut planes, density point clouds, segments, landmarks, etc. The cut planes, density point clouds, segments, landmarks, etc. are displayed virtually in correct location on the region of interest. In an embodiment, the information is displayed virtually with respect to the manual cutting guide, navigation cameras, navigation tracked tools, the robotic assembly, or other instruments for various surgical interventions or educational practices. The tracking feature further renders information such as at least one of surgery information, updated surgery information, and surgery notes. The information displayed may assist the surgeon while providing the treatment to the region of interest.

The virtual surgery generated alignment guide holds at least one of the cutting guide, the alignment guide, and the cutting tool via the second tool (as shown in FIG. 14b). The virtual surgery generated alignment guide further renders virtual measurements on the region of interest to guide manual surgery where robotic or other haptic solutions are used. The virtual surgery generated alignment guide further renders a measurement of a depth of a k-wire to be drilled down until a posterior end of the region of interest (e.g., tibia) is reached. The virtual measurements are displayed virtually. In an embodiment, the virtual measurements (e.g., depth of the k-wire) are added to physical incarnation of the virtual surgery generated alignment guide. The in-depth measurements added to the physical incarnation are useful for surgeon's knowledge. The in-depth measurements (seen in FIG. 14b) are adapted to mark a k-wire for length of plunge, etc. or as surgical notes prior to the procedure. The virtual surgery generated alignment guide further comprises a slot 1404. The slot enables anterior protrusion of the virtual surgery generated alignment guide from penetrating beyond the slot 1404. The slot 1404 is utilized to prevent a sawblade from plunging deeper than the anterior protrusion length of the region of interest (e.g., tibia). The slot is further adapted to prevent soft-tissue or artery damage. The slot 1404 is designed and prepared using a computer aided design (CAD) modelling. In an embodiment, the slot is designed and prepared using a cam shaft design. The slot 1404 allows only a mechanical object to move in and out through a curved surface.

FIGS. 15a and 15b illustrates a surface compliance device, according to one or more embodiments. The surface compliance device may be a glove worn by a user (e.g., surgeon) or a humanoid robot. The surface compliance device may be made of a flexible material, or a rigid material. In an embodiment, the surface compliance device is made of fabric. The surface compliance device enables the user to trace a surface of the region of interest. The surface compliance device is further adapted to determine locations of soft surfaces (e.g., soft tissue, ligaments, etc.) as well as rigid surfaces (e.g., bones) on the region of interest. The surface compliance device eliminates a need of computed tomography (CT) imaging or a magnetic resonance imaging (MRI) technique.

The surface compliance device (i.e., the glove) comprises one or more force sensors 1502 (as shown in FIG. 15a). The one or more force sensors 1502 may be embedded into a tactile region of the surface compliance device. The one or more force sensors 1502 generate closed loop information. The closed loop information may be generated by tracing the surface of the region of interest. The surface compliance device (i.e., the glove) comprises a tracking device 1504 at a wrist (as shown in FIG. 15b) of the surface compliance device. The tracking device 1504 may be a plurality of tracking devices. The tracking device 1504 is adapted to recognize and identify where the surgeon is examining relative to the anatomy. The surface compliance device may be used along with the system to register landmarks and eliminate external medical imaging.

The one or more force sensors 1502 of the surface compliance device are calibrated initially for each surgeon. Each surgeon may apply unique force or load on the region of interest while examining the region of interest during pre-surgery or post-surgery. The one or more force sensors 1502 determines the load or force applied by the surgeon on the region of interest. The surface compliance device then determines change in states at the region of interest such as ligament tensions or tissue stiffness. The change in the states is determined by comparing in-surgery force with the load or force applied by the surgeon. The tracing feature of the surface compliance device can be used to paint the features of the region of interest of the anatomy. The surface compliance device (e.g., glove) enables the user to paint the features using fingers and generate a computed tomography representation of the anatomy. The surface compliance device (e.g., glove) is also adapted to select landmark points and generate a point cloud information. The selected landmarks are utilized to register the region of interest in a virtual version. The virtual version of the region of interest can be used for landmark registration check and validate alignment guide assumptions.

In an embodiment, the surface compliance device can be utilized by the surgeon to examine a patient in a clinic for a baseline state. For example, the surgeon can perform a ligament draw test for ACL tension or integrity using the surface compliance device. In another embodiment, the surgeon can also perform soft tissue examinations like Hernia using the surface compliance device. The soft tissue examinations can be done by comparing landmarks of the soft tissue with the landmarks recorded in the database. The change in state can also be determined by comparing the state of the patient with appropriate healthy clustered state or unhealthy clustered state among the plurality of clusters of different physiological states.

The surface compliance device can also be used to determine varus/valgus tensioning for the region of interest (e.g., knee) in a surgery intervention. The varus/valgus tensioning is utilized to determine initial stability, post-surgical cuts, and implant or trial placement to determine the improved or maintained stiffness levels. The determined stiffness level is compared with similar patients who have undergone similar surgery or the patients who have been classified in a similar cluster. The determined stiffness level may also be compared with the stiffness level of the healthy person to determine whether the intervention is successful. The surface compliance device can also be used to conduct postop clinical examinations on the region of interest to determine at least one of recovery speed and intervention's success. The surgeon's clinical examination or surgery tests performed on the region of interest (e.g., soft tissues) can be correlated with the MRI or X-ray based imaging to calibrate evaluation of existing condition and post-surgery improved condition.

Figure 16:
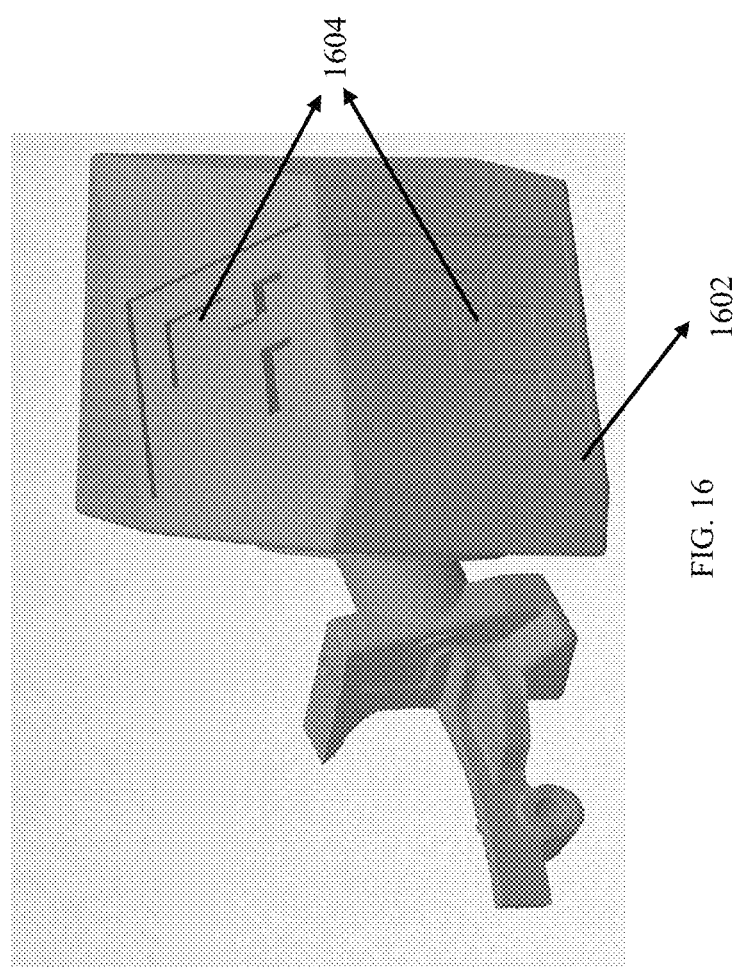
FIG. 16 illustrates an alignment guide comprising a printed tracking feature, according to one or more embodiments.

FIG. 16 illustrates an alignment guide 1602 comprising a printed tracking feature 1604, according to one or more embodiments. The printed tracking feature 1604 comprises one of a quick response (QR) code, a tracking code, radio wave frequencies, etc.). The alignment guide comprises the printed tracking feature embedded along with the alignment guide. The alignment guide and the printed tracking feature are not assembled, instead the alignment guide and the printed tracking feature are manufactured as a single piece. The printed tracking feature provides information, regarding at least one of depth, artery information, veins, tissue, and ligaments associated with a region of interest when scanned. The printed tracking feature further provides information regarding a tool associated with the virtual surgery generated alignment guide. The printed tracking feature further renders the information of at least one of the virtual measurements, surgery information, and updated surgery information to the user as treatment notes (e.g., surgical notes)

when a user scans the printed tracking feature. In an embodiment, the user can scan the printed tracking feature using a camera or a scanning device.

The printed tracking feature comprise right angled blocks that when tracked provides angulation information and the distance from the scanning device. In an embodiment, the printed tracking feature may comprise trapezoid blocks. The shape of the blocks depicts the treatment procedure (e.g., virtual cuts, planes, lines utilized for performing the treatment) on the region of interest.

The foregoing disclosure provides illustration and description but is not intended to be exhaustive or to limit the implementations to the precise form disclosed. Modifications and variations are possible in light of the above disclosure or may be acquired from practice of the implementations.

Those skilled in the art will appreciate that the invention may be practiced in network computing environments with many types of computer system configurations including personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, etc. The invention may also be practiced in distributed system environments where local and remote computer systems, which are linked (either by hardwired data links, wireless data links, or by a combination of hardwired and wireless data links) through a network, both perform tasks. In a distributed system environment, program modules or units may be located in both local and remote memory storage devices.

The present invention may be embodied in other specific forms without departing from its spirit or characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

Although the present embodiments have been described with reference to specific example embodiments, it will be evident that various modifications and changes may be made to these embodiments without departing from the broader spirit and scope of the various embodiments. For example, the various devices, units, and modules described herein may be enabled and operated using hardware circuitry (e.g., CMOS based logic circuitry), firmware, software or any combination of hardware, firmware, and software (e.g., embodied in a non-transitory machine-readable medium). For example, the various electrical structures and methods may be embodied using transistors, logic gates, and electrical circuits (e.g., application specific integrated (ASIC) circuitry and/or Digital Signal Processor (DSP) circuitry).

In addition, it will be appreciated that the various operations, processes, and methods disclosed herein may be embodied in a non-transitory machine-readable medium and/or a system. Accordingly, the specification and drawings are to be regarded in an illustrative rather than a restrictive sense.

INCORPORATION BY REFERENCE

All publications, patents, and patent applications cited in this Specification are hereby incorporated by reference in their entirety, including:

US20140093153A1 entitled "Method and System for Bone Segmentation and Landmark Detection for Joint Replacement Surgery";

US20190005186A1 entitled "Systems and methods for using generic anatomy models in surgical planning";

WO2020141812A1 entitled "Region of interest labeling device for bone marrow interpretation, and region of interest detection system comprising same";

EP2754419A2 entitled "Patient-adapted and improved orthopedic implants, designs and related tools";

EP1716535A2 entitled "Virtual endoscopy methods and systems";

US20150328004 entitled "Bone Reconstruction and Orthopedic Implants";

U.S. Pat. No. 9,452,050B2 entitled "Method incorporating computer-implemented steps, a computing device and a computer readable storage medium for developing manufacturing parameters for manufacturing an orthopaedic implant";

U.S. Ser. No. 10/292,770B2 entitled "Systems, methods, and devices for developing patient-specific spinal treatments, operations, and procedures";

U.S. Ser. No. 10/595,844B2 entitled "Systems and methods for surgical and interventional planning, support, post-operative follow-up, and functional recovery tracking";

US20080221923A1 entitled "Medical information management system";

WO2020037308A1 entitled "Patient-specific surgical method and system";

US20190183411A1 entitled "Virtual Ligament Balancing";

US20200205898A1 entitled "Systems and methods for surgical planning using soft tissue attachment points";

US20200170604A1 entitled "CT Based Probabilistic Cancerous Bone Region Detection";

U.S. Ser. No. 10/582,970B2 entitled "System and method for predicting tissue integrity"; and U.S. Ser. No. 17/025,458 entitled "Patient Specific Treatment Planning".

What is claimed is:

1. A method comprising:
receiving an image file of a region of interest of an anatomy of a living organism;
analyzing the image file and extracting image coordinates and density information of a plurality of points in the image file;
training a neural network using collective information available in a database, wherein the collective information is recorded in the database with respect to a plurality of clusters of different physiological states of the living organism;
registering the region of interest of the anatomy as a virtual version using an input from the neural network;
subsequently training the neural network using a user input from a user and the collective information available in the database;
measuring the virtual version of the region of interest using a virtual measurement tool; and
rendering virtual measurements and a treatment plan of the region of interest, wherein rendering the virtual measurements and the treatment plan enables the user to one of mark surgical measurements and make surgical notes prior to the treatment.

2. The method of claim 1, wherein registering the region of interest as the virtual version enables:

recommending at least one of a treatment procedure, a treatment plan, and a treatment location of the region of interest based on the collective information in the database.

3. The method of claim 2, wherein recommending at least one of the treatment procedure, the treatment plan, and the treatment location of the region of interest based on the collective information in the database comprises:
creating the treatment plan to at least one of reach and approach of an area of interest and an object within the region of interest in six degrees of freedom via a path through at least one of invasive route, and partially invasive route; and
recommending the treatment plan to at least one of an automated machine, a semi-automated machine, and a surgeon to perform the treatment.

4. The method of claim 3, wherein creating the treatment plan comprises automatically generating the path, by the neural network, that guide one of the automated machine, the semi-automated machine, and the surgeon to at least one of reach and approach of the area of interest and the object within the region of interest, the path comprises at least one of a straight path, a regular path, a curved path, and an irregular path.

5. The method of claim 4, further comprises:
training the neural network using engineering safety rules and surgeon prescribed rules to generate the path to at least one of reach and approach of the area of interest and the object within the region of interest.

6. The method of claim 1, further comprising:
creating a virtual surgery generated alignment guide based on tracking a three-dimensional physical incarnation of the region of interest and recognizing a first color and a first identifier, and a second color and a second identifier on the three-dimensional physical incarnation.

7. The method of claim 6, further comprising:
generating a virtual version of the virtual surgery generated alignment guide, wherein the virtual version of the virtual surgery generated alignment guide comprises at least one of a two-dimensional virtual surgery generated alignment guide and a three-dimensional virtual surgery generated alignment guide.

8. The method of claim 7, further comprising:
virtually attaching the virtual version of the virtual surgery generated alignment guide to a physiological feature at a first location in the region of interest where a surgical incision has created enough opening to expose medical image predicted surface on the region of interest.

9. The method of claim 8, further comprising:
analyzing, using the neural network, the virtual attachment of the virtual surgery generated alignment guide on the physiological feature;
creating a physical version of the virtual surgery generated alignment guide; and
physically attaching the virtual surgery generated alignment guide to the physiological feature at the first location in the region of interest based on the analyzing performed.

10. The method of claim 6, wherein the virtual surgery generated alignment guide comprises a coupling feature adapted to couple at least one external attachment with the virtual surgery generated alignment guide mechanically and electronically.

11. The method of claim 7, wherein the virtual version of the virtual surgery generated alignment guide appropriately fits the region of interest of the anatomy and enables effective and instant registration of a location and an orientation of the region of interest in relation to a second region of interest of the anatomy.

12. The method of claim 6, wherein creating the virtual surgery generated alignment guide comprises a slot with an anterior protrusion tool to prevent a saw blade from plunging deeper than a length of an anterior protrusion of the region of interest to prevent at least one of soft-tissue damage and artery damage.

13. A system comprising:
a server, wherein the server comprises a processor, and a memory communicatively coupled to the processor, the processor is operable to
receive an image file of a region of interest of an anatomy of a living organism;
analyze the image file and extract image coordinates and density information of a plurality of points in the image file;
train a neural network using collective information available in a database, wherein the collective information is recorded in the database with respect to a plurality of clusters of different physiological states of the living organism;
register the region of interest of the anatomy as a virtual version using an input from the neural network; and
subsequently train the neural network using a user input from a user and the collective information available in the database; and
a virtual surgery generated alignment guide that comprises
a first tool adapted to identify and match the region of interest in relation to the anatomy;
a second tool adapted to hold and fasten an external instrument; and
a third tool adapted to hold and affix an alignment guide.

14. The system of claim 13, further comprising:
a surface compliance device that comprises
a force sensor operable to generate closed loop information of the region of interest; and
a tracking device operable to track at least one of a location, and a position of the region of interest at which the surface compliance device is in contact with the region of interest.

15. The system of claim 14, wherein the surface compliance device comprises a glove held by the user operable to at least one of trace a surface of the region of interest and paint a feature of the region of interest.

16. The system of claim 13, wherein the virtual surgery generated alignment guide comprises at least one of a printed tracking feature and a detectable wave frequency.

17. The system of claim 16, wherein the printed tracking feature comprises one of a tracking code and a quick response (QR) code, wherein the printed tracking feature provides information of at least one of depth, arteries, veins, tissues, ligaments of the region of interest and a tool associated with the virtual surgery generated alignment guide.

18. A non-transitory computer storage medium storing a sequence of instructions, which when executed by a processor, causes:
receiving an image file of a region of interest of an anatomy of a living organism;
analyzing the image file and extracting image coordinates and density information of a plurality of points in the image file;

training a neural network using collective information available in a database, wherein the collective information is recorded in the database with respect to a plurality of clusters of different physiological states of the living organism;

registering the region of interest of the anatomy as a virtual version using an input from the neural network;

subsequently training the neural network using a user input from a user and the collective information available in the database;

measuring the virtual version of the region of interest using a virtual measurement tool; and rendering virtual measurements and a treatment plan of the region of interest, wherein rendering the virtual measurements and the treatment plan enables the user to one of mark surgical measurements and make surgical notes prior to the treatment.

* * * * *